United States Patent
Lim et al.

(10) Patent No.: US 9,862,985 B2
(45) Date of Patent: Jan. 9, 2018

(54) IDENTIFICATION AND SUSCEPTIBILITY OF MICROORGANISMS BY SPECIES AND STRAIN

(71) Applicant: SPECIFIC TECHNOLOGIES LLC, West Palm Beach, FL (US)

(72) Inventors: Sung Hyun Lim, Mountain View, CA (US); Raymond Anthony Martino, Los Gatos, CA (US); Paul A. Rhodes, Woodside, CA (US)

(73) Assignee: Specific Technologies LLC, West Palm Beach, FL (US)

( * ) Notice: Subject to any disclaimer, the term of this patent is extended or adjusted under 35 U.S.C. 154(b) by 93 days.

(21) Appl. No.: 14/396,685

(22) PCT Filed: Apr. 26, 2013

(86) PCT No.: PCT/US2013/038513
§ 371 (c)(1),
(2) Date: Oct. 23, 2014

(87) PCT Pub. No.: WO2013/163610
PCT Pub. Date: Oct. 31, 2013

(65) Prior Publication Data
US 2015/0099694 A1 Apr. 9, 2015

Related U.S. Application Data

(60) Provisional application No. 61/639,556, filed on Apr. 27, 2012.

(51) Int. Cl.
*C12Q 1/04* (2006.01)
*C12Q 1/18* (2006.01)
*C40B 30/02* (2006.01)
*G01N 33/497* (2006.01)

(52) U.S. Cl.
CPC .......... *C12Q 1/04* (2013.01); *C12Q 1/18* (2013.01); *C40B 30/02* (2013.01); *G01N 33/497* (2013.01); *C12Q 2304/40* (2013.01); *G01N 2800/52* (2013.01)

(58) Field of Classification Search
None
See application file for complete search history.

(56) References Cited

U.S. PATENT DOCUMENTS

| 6,368,558 | B1 | 4/2002 | Suslick et al. |
| 6,495,102 | B1 | 12/2002 | Suslick et al. |
| 7,261,857 | B2 | 8/2007 | Suslick et al. |
| 2003/0143112 | A1 | 7/2003 | Suslick et al. |
| 2005/0171449 | A1 | 8/2005 | Suslick et al. |
| 2008/0199904 | A1* | 8/2008 | Suslick ............ C12Q 1/04 435/34 |
| 2010/0166604 | A1 | 7/2010 | Lim et al. |

FOREIGN PATENT DOCUMENTS

| GB | WO 2006079846 A1 * | 8/2006 | ............ C12Q 1/04 |
| WO | WO2009054913 A1 | 4/2009 | |
| WO | WO2010028057 A1 | 3/2010 | |
| WO | WO2013163610 A1 | 10/2013 | |

OTHER PUBLICATIONS

International Search Report and Written Opinion for International Application No. PCT/US2013/038513, dated Jul. 23, 2013, 15 pages.
Koo et al., "Fluorescent DNA chemosensory: identification of bacterial species by their volatile metabolites," Chemical Communication (2011), vol. 47, pp. 11435-11437.
Carey et al., "Rapid Identification of Bacteria with a Disposable Colorimetric Sensing Array," Journal of the American Chemical Society (2011), vol. 133, pp. 7571-7576.
European Examination Report for Application No. 13781258.2, dated Jan. 14, 2016, 4 pages.
European Search Report for Application No. 13781258.2, dated Dec. 18, 2015, 6 pages.
S. H. Lim et al: "Colorimetric Sensor Array Allows Fast Detection and Simultaneous Identification of Sepsis-Causing Bacteria in Spiked Blood Culture" Journal of Clinical Microbiology, vol. 52, No. 2, Feb. 11, 2014, pp. 592-598.
European Examination Report for Application No. 13781258.2, dated Nov. 15, 2016, 4 pages.

\* cited by examiner

*Primary Examiner* — Robert Yamasaki
*Assistant Examiner* — Charles Zoltan Constantine
(74) *Attorney, Agent, or Firm* — Fish & Richardson P.C.

(57) ABSTRACT

Devices, systems, and methods for strain-specific identification and assessment of susceptibility of microorganisms based on the response of sensors in a colorimetric sensor array to metabolic products of the microorganism.

26 Claims, 9 Drawing Sheets

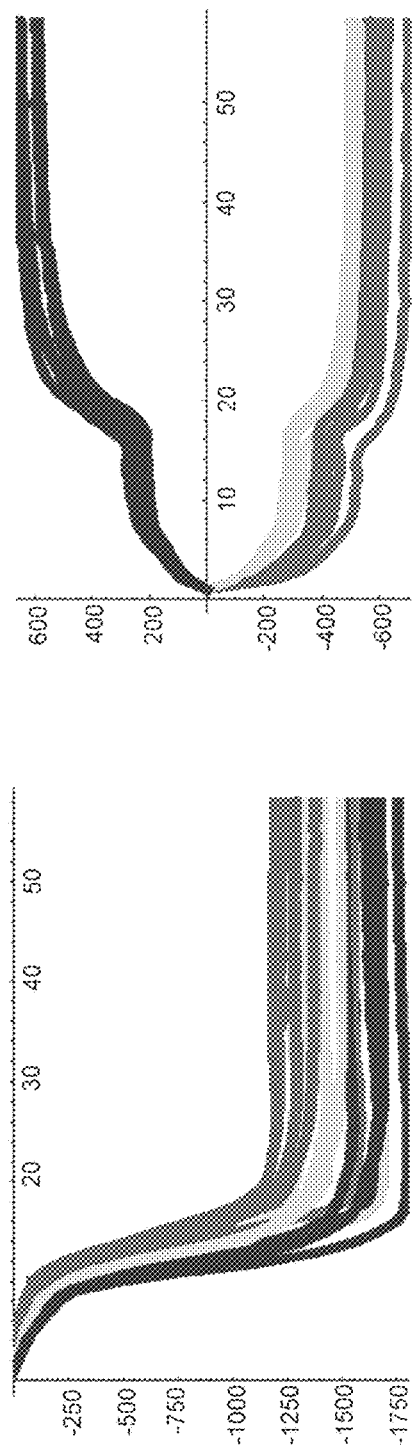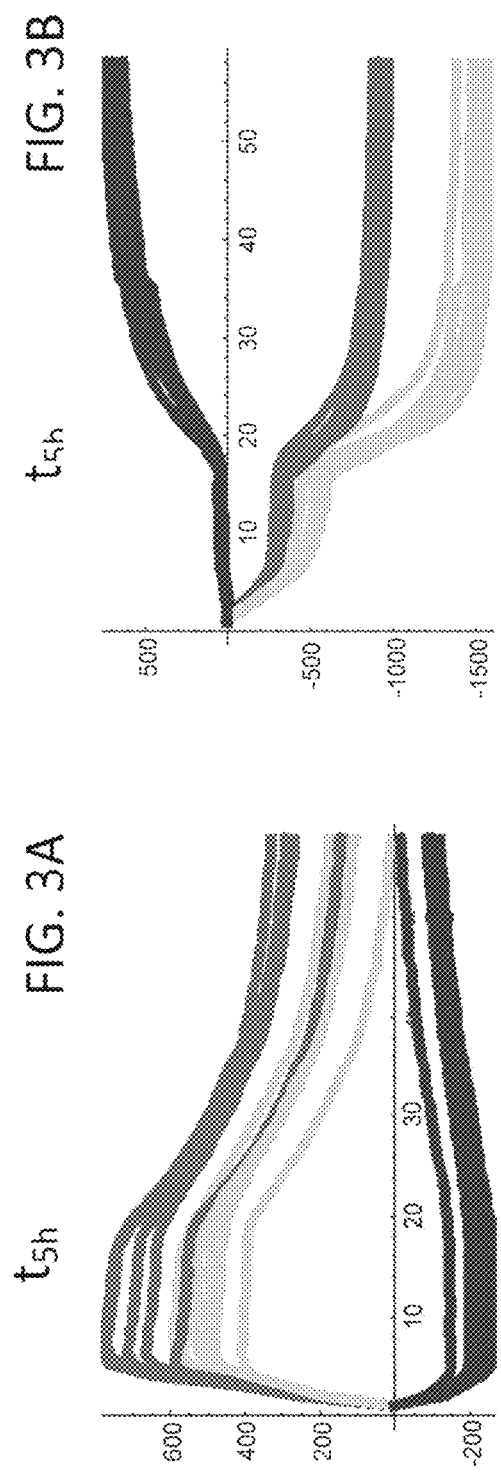

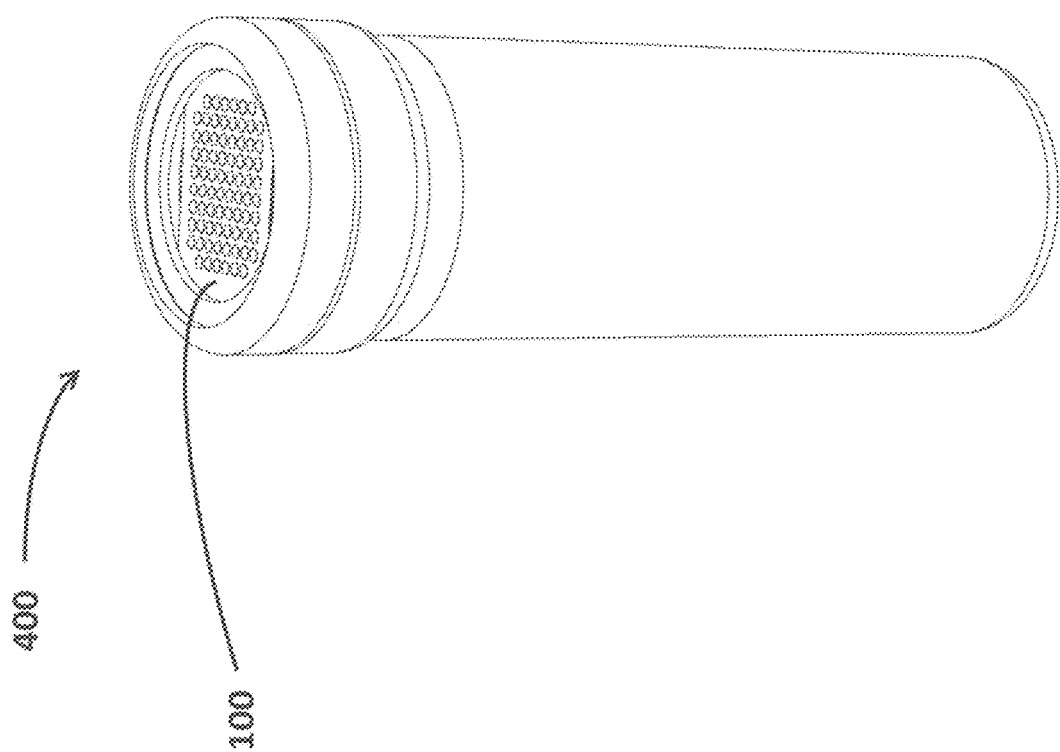

US 9,862,985 B2

IDENTIFICATION AND SUSCEPTIBILITY OF MICROORGANISMS BY SPECIES AND STRAIN

CROSS-REFERENCE TO RELATED APPLICATION APPLICATIONS

This application is a National Stage Application of International Application No. PCT/US2013/038513 filed Apr. 26, 2013, which claims the benefit of U.S. Provisional Application Ser. No. 61/639,556 filed on Apr. 27, 2012, the contents of both of which are incorporated herein by reference in their entirety.

FIELD OF THE INVENTION

This disclosure is related to identifying microorganism species and strain and determining the strain antibiotic resistance and the antibiotic susceptibility of microorganisms.

BACKGROUND

Antibiotic susceptibility is typically determined in three-day process that includes an average two-day plate growth phase followed by a susceptibility test in an automatic scanner. In some cases, effective antibiotic treatment of a patient may not begin until susceptibility is assessed. Thus, reducing the amount of time required to identify species and strain and strain resistance to antibiotics and to assess antibiotic susceptibility would be advantageous.

SUMMARY

A first general aspect includes culturing a sample including a microorganism in the presence of a colorimetric sensor array, thereby exposing sensors in the colorimetric sensor array to volatile organic compounds produced by the microorganism, identifying the microorganism by species and strain based on the response of the sensors in the colorimetric sensor array to the volatile organic compounds produced by the microorganism, and assessing susceptibility of the microorganism to a substance based on the response of the sensors in the colorimetric sensor array to the volatile organic compounds produced by the microorganism.

A second general aspect is related to reducing a population of a selected microorganism in a mammal carrying the microorganism, and includes collecting a sample including at least one of the selected microorganisms from the mammal, culturing the microorganism(s) in the presence of a colorimetric sensor array, thereby exposing sensors in the colorimetric sensor array to volatile organic compounds produced by the microorganism(s), identifying susceptibility of the microorganism(s) to a substance based on the response of the sensors in the colorimetric sensor array to the volatile organic compounds produced by the microorganism(s), and administering a dose of the substance to the mammal, wherein the dose is effective to reduce the population of the identified microorganism in the mammal.

A third general aspect is related to reducing a bacterial population in a mammal showing symptoms of infection, and includes collecting a sample of bacteria from the mammal, culturing some of the bacteria in the presence of a colorimetric sensor array, thereby exposing sensors in the colorimetric sensor array to volatile organic compounds produced by the bacteria, identifying susceptibility of the bacteria to a substance based on the response of the sensors in the colorimetric sensor array to the volatile organic compounds produced by the bacteria, and administering a dose of the substance to the mammal, wherein the dose is effective to reduce the number of the identified bacteria in the mammal.

A fourth general aspect includes culturing a sample comprising a species of bacteria in the presence of a colorimetric sensor array, thereby exposing sensors in the colorimetric sensor array to volatile organic compounds produced by the bacteria, and identifying the bacteria by species and strain based on the response of the sensors in the colorimetric sensor array to the volatile organic compounds produced by the bacteria, wherein identifying the bacteria by species and strain comprises identifying a substance-resistant strain of a species of bacteria.

Implementations of the general aspects may include one or more of the following features.

The microorganism may be identified by species and strain (e.g., based on the response of the sensors in the colorimetric sensor array to the volatile organic compounds produced by the bacteria) before identifying the susceptibility of the bacteria to the substance. Identifying the bacteria by species and strain may include identifying an antibiotic-resistant mutant.

The microorganism may be collected from a substrate before culturing the microorganism. The substrate may be, for example, woven or nonwoven fabric, paper, metal, or plastic.

In some cases, the microorganism is collected from a mammal (e.g., a human) before culturing the microorganism. Collecting the microorganism from the mammal may include collecting a fluid sample or a tissue sample from the mammal, wherein the fluid sample comprises a gas (e.g., exhaled breath), a liquid (e.g., blood), or a combination thereof. The mammal may be showing symptoms of bacteremia.

A substance to which the microorganism is susceptible may be identified based on the response of the sensors in the colorimetric sensor array to the volatile organic compounds produced by the microorganism. The substance may be, for example, a medication approved for use by animals or humans. The substance may be selected based on the identified species and strain of the microorganism (e.g., bacteria). In some cases, a dose of the substance is administered to the mammal from which the microorganism was collected, wherein the dose is effective to reduce the number of the identified microorganisms in the mammal.

In some cases, susceptibility of the microorganism to the substance may be assessed within 64 hours, within 48 hours, within 36 hours, within 24 hours, within 12 hours, within 10 hours within 8 hours, within 6 hours, or within 4 hours after identification of the microorganism.

In certain cases, culturing the bacteria includes culturing the bacteria on a solid medium or in a liquid medium. The response of each sensor may include a change in one or more color components of the sensor. The temporal and/or static response of the sensors may yield a temporal or static color response pattern of the bacteria. Identifying the bacteria by species and strain may include comparing the temporal and/or static color pattern of the bacteria with a library of temporal and/or static color response patterns characteristic of known strains of bacteria.

Susceptibility of the bacteria to a substance may be assessed based on the response of the sensors in the colorimetric sensor array to the volatile organic compounds produced by the bacteria. A does of a substance to which the bacteria is susceptible may be administered to the mammal from which the bacteria was collected, the dose being effective to reduce the number of the identified bacteria in the mammal.

Advantages described herein include species identification and susceptibility assay to be complete less than 24 hours after samples reach the laboratory.

BRIEF DESCRIPTION OF DRAWINGS

FIGS. 3A-3D show the temporal response of four different sensors in the colorimetric sensor array shown in FIGS. 2A-2C.

FIG. 4 depicts a container including a colorimetric sensor array.

DETAILED DESCRIPTION

Figure 1:
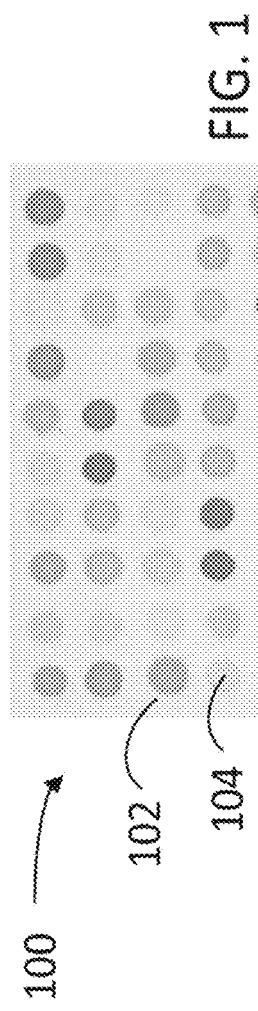
FIG. 1 depicts a colorimetric sensor array.

A colorimetric sensor is a sensor that includes one or more materials that undergo a change in spectral properties upon exposure to an appropriate change in the environment of the sensor. The change in spectral properties may include a change in the absorbance, fluorescence and/or phosphorescence of electromagnetic radiation, including ultraviolet, visible and/or infrared radiation. Culturing a sample including a microorganism (e.g., a species of bacteria) in the presence of a colorimetric sensor array exposes sensors in the colorimetric sensor array to volatile organic compounds produced by the microorganism. U.S. Patent Publication No. 2008/0199904 to Suslick et al., U.S. Patent Publication No. 2010/0166604 to Lim et al., and Carey et al., "Rapid Identification of Bacteria with a Disposable Colorimetric Sensing Array," J. Am. Chem. Soc. 2011, 133, 7571-7576, all of which are incorporated by reference herein, describe identification of bacteria from volatiles they produce using colorimetric sensor arrays. Response of the sensors in the colorimetric sensor array to the volatile organic compounds yields a strain-specific temporal or static color response pattern, allowing the microorganism to be identified by comparison of the color response pattern with color response patterns for known strains. Comparison may be achieved, for example, visually or automatically by methods generally known in the art.

While bacteria of a given species share certain characteristics, different strains of the same species yield noticeably different color response patterns (or "fingerprints"), allowing discrimination between strains of the given species (e.g., between *Staphylococcus aureus* and methicillin-resistant *Staphylococcus aureus* and between *Enterococus faecalis* and vancomycin-resistant *Enterococus faecalis*). The color response patterns allow identification of microorganisms by species and strain and certain antibiotic resistant characteristics in a fraction of the time (e.g., about three-quarters of the time, about one-half of the time, or about one-quarter of the time) of other methods, based at least in part on conditions such as concentration, culture medium, culture conditions (e.g., temperature), and the like.

In addition, colorimetric sensor arrays can be also used to assess susceptibility of a microorganism (e.g., a microorganism identified based on the response of the sensors in a first colorimetric sensor array to the volatile organic compounds produced by the microorganism) to a substance, such as a drug approved for use by humans. In some cases, susceptibility can be assessed in a matter of hours (e.g., less than twelve hours, less than ten hours, less than 8 hours, or less than 6 hours) after identification of the microorganism. This sequence of identification and assessment of susceptibility allows rapid treatment of patients experiencing a malady (e.g., sepsis, meningitis, etc.) related to a pathogenic microorganism. In some cases, susceptibility of a microorganism is assessed without prior identification of the microorganism.

Microorganisms such as bacteria, yeasts, protozoa, and fungi can be identified as described herein. Species of bacteria that can be identified include, for example, *Staphylococcus aureus, Staphylococcus epidermidis, Staphylococcus sciuri, Pseudomonas aeruginosa, Enterococcus faecium, Enterococcus faecalis, Escherichia coli, Klebsiella pneumoniae, Streptococcus pneumoniae, Streptococcus pyrogenes, Vibrio cholera, Achromobacter xylosoxidans, Burkholderia cepacia, Citrobacter diversus, Citrobacter freundii, Micrococcus leuteus, Proteus mirabilis, Proteus vulgaris, Staphylococcus lugdunegis, Salmonella typhi, Streptococcus* Group A, *Streptococcus* Group B, *S. marcescens, Enterobacter cloacae, Bacillus anthracis, Bordetella pertussis, Clostridium* sp., *Clostridium botulinum, Clostridium tetani, Corynebacterium diphtheria, Moraxalla (Brauhamella) catarrhalis, Shigella* spp., *Haemophilus influenza, Stenotrophomonas maltophili, Pseudomonas perolens, Pseuomonas fragi, Bacteroides fragilis, Fusobacterium* sp. *Veillonella* sp., *Yersinia pestis,* and *Yersinia pseudotuberculosis*. Strains of bacteria that can be identified include, for example, *S. aureus* 25923, *S. aureus* 29213, *S. aureus* 43300, *S. aureus* IS-13, *S. aureus* IS-38, *S. aureus* IS-43, *S. aureus* IS-70, *S. aureus* IS-120, *S. aureus* IS-123, *S. aureus* IS-124, methicillin-resistant *S. aureus* 33591, *S. epidermidis* 35984, *S. sciuri* 49575, *P. aeruginosa* 10145, *P. aeruginosa* IS-15, *P. aeruginosa* IS-65, *P. aeruginosa* IS-22, *P. aeruginosa* IS-36, *P. aeruginosa* 27853, *E. faecium* 19434, *E. faecalis* 23241, vancoymcin-resistant *E. faecalis* 51299, *E. coli* 25922, *E. coli* 53502, *E. coli* 35218, *E. coli* 760728, *E. coli* IS-39, *E. coli* IS-44, *A. xylosoxidans* IS-30, *A. xylosoxidans* IS-35, *A. xylosoxidans* IS-46, *A. xylosoxidans* IS-55, *C. diversus* IS-01, *C. diversus* IS-28, *C. diversus* IS-31, *C. diversus* IS-33, *K. pneumoniae* IS-130, *K. pneumoniae* IS-133, *K. pneumoniae* IS-136, *K. pneumoniae* 33495, *B. anthrax* Ames, *B. anthrax* UM23CL2, *B. anthrax* Vollum, *Y. pestis* CO92, *Y. pestis* Java 9, *S. epidermis* 12228, *S. epidermis* IS-60, *S. epidermis* IS-61, *P. miribilis* IS-18, *P. miribilis* IS-19, *P. miribilis* 12453, *S. marcescens* IS-48, *S. marcescens* IS-05, and *S. marcescens* 13880, where "IS-#" refers to clinical isolates and the other strains are ATCC® reference strains. Species of fungi that can be identified include, for example, *Microsporum* sp. *Trichophyton* sp. *Epidermophyton* sp., *Sporothrix schenckii*, *Wangiella dermatitidis*, *Pseudallescheria boydii*, *Madurella grisea*, *Histoplasma capsulatum*, *Blastomyces dermatitidis*, *Coccidioides immitis*, *Cryptococcus neoformans*, *Aspergillus fumigatus*, *Aspergillus niger*, and *Candida albicans*. Similarly, yeasts including Ascomycota (Saccharomycotina, Taphyrinomycotina, Schizosaccharomycetes) and Basidiomycota (Agaricomycotina, Tremellomycetes, Pucciniomycotina, Microbotryomycetes) can be identified and, if desired, assessed for susceptibility. Examples include *Saccharomyces cerevisiae* and *Candida albicans*. Protozoa including flagellates (e.g., *Giardia lamblia*), amoeboids (e.g., *Entamoeba histolytica*), sporozoans (e.g., *Plasmodium knowlesi*), and ciliates (e.g., *Balantidium coli*) may also be identified as described herein.

Colorimetric sensor arrays described herein can be used to identify and/or monitor pathogenic and non-pathogenic microorganisms. In one example, a sample including microorganisms from a mammal (e.g., a human) showing symptoms a malady or in need of treatment for a malady can be taken from the mammal (e.g., in the form of a fluid sample such as blood or exhaled breath, or in the form of a tissue sample) and cultured in the presence of a colorimetric sensor array. In other examples, microorganisms such as *Saccharomyces cerevisiae* and others can be monitored in processes such as baking and alcoholic fermentation processes, electricity generation in microbial fuel cells, and biofuel production.

FIG. 1 depicts an exemplary colorimetric sensor array 100. Colorimetric sensor array 100 includes a substrate 102 having a multiplicity of colorimetric sensors 104, each colorimetric sensor including an indicator selected to change color in the presence of at least one volatile organic compound. Colorimetric sensor arrays typically include an array of chemoresponsive colorants, where the colors of the chemoresponsive colorant are affected by a wide range of analyte-dye interactions. "Chemoresponsive colorant" refers to any material that absorbs, reflects, and/or emits light when exposed to higher frequency electromagnetic radiation. A light-absorbing portion of a chemical indicator is referred to as a chromophore, and a light-emitting portion of a colorant is referred to as a fluorophore. "Chemoresponsive colorant" generally refers to an indicator that undergoes a change in spectral properties in response to an appropriate change in its chemical environment. "Change in spectral properties" generally refers to a change in the frequency and/or intensity of the light the colorant absorbs and/or emits. Chemoresponsive colorants include dyes and pigments.

Examples of chemoresponsive dyes include Lewis acid-base dyes, metalloporphyrins, free base porphyrins, phthalocyanines, pH sensitive dyes, solvatochromic dyes, vapochromic dyes, redox sensitive dyes, and metal ion sensitive dyes. Chemoresponsive dyes may be responsive to one or more chemical interactions including Lewis acid-base interaction, Brønsted acid-base interaction, ligand binding, π-π complexation, hydrogen bonding, polarization, oxidation/reduction, and metal coordination.

The chemoresponsive dye may be, for example, a Lewis acid-base dye, such as a Lewis acid dye or a Lewis base dye. A Lewis acid-base dye is a dye that can interact with a substance by acceptor-donor sharing of a pair of electrons with the substance, resulting in a change in spectral properties. The change in spectral properties for a Lewis acid-base dye may be related to Lewis acid-base interaction and ligand binding, but also to π-π complexation, hydrogen bonding, and/or polarity changes. Lewis acid-base dyes include metal-ion containing dyes, such as metalloporphyrins and other metal ion ligating macrocycles or chelating dyes; boron- and boronic acid containing dyes; and dyes with accessible heteroatoms (e.g., N, O, S, P) with lone electron pairs capable of Lewis coordination (e.g., "complexometric dyes").

Examples of Lewis acid-base dyes include metal ion-containing dyes, such as metal ion-containing porphyrins (i.e., metalloporphyrins), salen complexes, chlorins, bispocket porphyrins, and phthalocyanines. Diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). In one example, a parent porphyrin is the so-called free base form 5,10,15,20-tetraphenylporphyrin ($H_2TPP$), its dianion is 5,10,15,20-tetraphenyl-porphyrinate(−2) (TPP dianion), its metalated complexes, and its acid forms ($H_3TPP^+$ and $H_4TPP^{+2}$). This porphyrin may form metalated complexes, for example, with $Sn^{4+}$, $Co^{3+}$, $Co^{2+}$, $Cr^{3+}$, $Mn^{3+}$, $Fe^{3+}$, $Cu^{2+}$, $Ru^{2+}$, $Zn^{2+}$, $Ag^{2+}$, $In^{3+}$, and $Ir^{3+}$. Metal ion-containing metalloporphyrin dyes are described, for example, in U.S. Pat. No. 6,368,558 to Suslick et al. and in U.S. Patent Application Publication No. 2003/0143112 to Suslick et al., both of which are incorporated by reference herein.

Visible spectral shifts and absorption intensity differences for metalloporphyrins may occur upon ligation of the metal center, leading to readily observable changes in spectral properties. The magnitude of this spectral shift typically correlates with the polarizability of the ligand, thus allowing for distinction between analytes based on the electronic properties of the analytes. Using metal centers that span a range of chemical hardness and ligand binding affinity, it may be possible to differentiate between a wide range of volatile analytes, including molecules having soft functional groups such as thiols, and molecules having hard functional groups such as amines. Because porphyrins can exhibit wavelength and intensity changes in their absorption bands with varying solvent polarity, an array that includes porphyrins may be used to colorimetrically distinguish among a series of weakly coordinating solvent vapors, such as arenes, halocarbons and ketones.

The chemoresponsive dye may be, for example, a structure-sensitive porphyrin. Structure-sensitive porphyrins include modified porphyrins that include a super structure bonded to the periphery of the porphyrin. For example, metalloporphyrins functionalized with a super structure at the periphery may limit steric access to the metal ion, allowing for shape-selective distinction of analytes, such as between n-hexylamine and cyclohexylamine. Controlling the ligation of various nitrogenous ligands to dendrimer-metalloporphyrins can provide for selectivities over a range of more than $10^4$.

Examples of super structures that may be bonded to a porphyrin include dendrimers, siloxyl groups, aryl groups such as phenyl groups, alkyl groups such as t-butyl groups, organometallic groups, inorganic groups, and other bulky substituents. Porphyrins bearing super structures may be selective to molecular shape, including sensitivity to steric factors, enantiomeric factors, and regioisomeric factors. For example, the structures may provide sterically constrained pockets on one or both faces of the porphyrin. Porphyrins bearing super structures also may be sensitive to factors such as hydrogen bonding and acid-base functionalities. Metal ion-containing metalloporphyrin dyes that include a super structure bonded to the periphery of the porphyrin, and methods of making such dyes, are disclosed, for example, in U.S. Pat. No. 6,495,102 to Suslick et al., which is incorporated by reference herein.

One example of modified porphyrins that include a super structure bonded to the periphery of the porphyrins is the family of tetrakis(2,4,6-trimethoxyphenyl)-porphyrin (TT-MPP). By varying the metal in this porphyrin, it is possible to distinguish between substances such as between t-butylamine and n-butylamine, and between cyclohexylamine and n-hexylamine. Another example of a modified porphyrin that includes a super structure bonded to the periphery of the porphyrin is the family of silylether-metalloporphyrins. For example, scaffolds derived from the reaction of 5,10,15,20-tetrakis(2',6'-dihydroxyphenyl)-porphyrinatozinc(II) with t-butyldimethylsilyl chloride provide Zn(II) porphyrin having in which the two faces are protected with six, seven, or eight siloxyl groups. This can result in a set of three porphyrins having similar electronic properties, but having different hindrance around the central metal atom present in the porphyrin. The shape selectivities of these porphyrins may be up to $10^7$ or greater.

Other examples of modified porphyrins that include a super structure bonded to the periphery of the porphyrin include siloxyl-substituted bis-pocket porphyrins, such as 5-phenyl-10,15,20-tris(2',6'-dihydroxyphenyl)porphyrinatozinc(II); 5,10,15,20-tetrakis(2',6'-dihydroxyphenyl)porphyrinatozinc(II); 5(phenyl)-10,15,20-trikis(2',6'-disilyloxyphenyl)porphyrinatozinc(II); 5,10,15-trikis(2',6'-disilyloxyphenyl)-20-(2'-hydroxy-6'-silyloxyphenyl) porphyrinatozinc(II). The shape selectivities of these porphyrins may be up to $10^7$ or greater compared to unhindered metalloporphyrins. Fine-tuning of ligation properties of these porphyrins may be possible, such as by using pockets of varying steric demands.

Other examples of metal ion-containing metalloporphyrin dyes that include a super structure bonded to the periphery of the porphyrin include 2,3,7,8,12,13,17,18-octafluoro-5,10,15,20-tetrakis(pentafluorophenyl)-porphyrinatocobalt (II); 2,3,7,8,12,13,17,18-octabromo-5,10,15,20-tetraphenyl-porphyrinatozinc (II); 5,10,15,20-tetraphenylporphyrinatozinc(II); 5(phenyl)-10,15,20-trikis (2',6'-bis(dimethyl-t-butylsiloxyl)phenyl)porphyrinatozinc (II); 5,10,15,20-tetrakis(2',6'-bis(dimethyl-t-butylsiloxyl) phenyl)porphyrinatozinc(II); 5,10,15,20-tetraphenylporphyrinatocobalt (II); 5,10,15,20-tetrakis(2,6-difluorophenyl)-porphyrinatozinc(II); and 5,10,15,20-tetrakis(2,4,6-trimethylphenyl)-porphyrinatozinc(II).

An array that includes a structure-sensitive porphyrin may be used in combinatorial libraries for shape selective detection of substrates. Such an array also may include a structure-sensitive having chiral super structures on the periphery of the porphyrin, which may provide for identification of chiral substrates, such as drugs, natural products and components of biological samples from a patient. Such an array also may be used for analysis of biological entities based on the surface proteins, oligosaccharides, antigens, etc., that interact with the metalloporphyrins. Examples of biological entities include individual species of bacteria and viruses. Such an array also may be used for analysis of nucleic acid sequences, including specific recognition of individual sequences of nucleic acids. Substituents on the porphyrins that would be particularly useful in this regard include known DNA intercalating molecules and nucleic acid oligomers.

The chemoresponsive dye may be, for example, a pH sensitive dye. Dyes that are pH sensitive include pH indicator or acid-base indicator dyes that may change color upon exposure to acids or bases. Examples of pH sensitive dyes include Brønsted acid dyes. A Brønsted acid dye is a proton donor that can donate a proton to a Brønsted base (i.e., a proton acceptor), resulting in a change in spectral properties. Under certain pH conditions, a Brønsted acid dye may be a Brønsted base.

Examples of Brønsted acid dyes include protonated, but non-metalated, porphyrins; chlorines; bispocket porphyrins; phthalocyanines; and related polypyrrolic dyes. Examples of non-metalated porphyrin Brønsted acid dyes include 5,10,15,20-tetrakis(2',6'-bis(dimethyl-t-butylsiloxyl)phenyl)porphyrin dication; 5,10,15,20-tetraphenyl-21H,23H-porphyrin; or 5,10,15,20-tetraphenylporphyrin dication. Other examples of Brønsted acid dyes include Chlorophenol Red, Bromocresol Green, Bromocresol Purple, Bromothymol Blue, Bromopyrogallol Red, Pyrocatechol Violet, Phenol Red, Thymol Blue, Cresol Red, Alizarin, Mordant Orange, Methyl Orange, Methyl Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange #25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, Malachite Green Carbinol Base, Nile Red, Nile Blue, Nitrazine Yellow, Bromophenol Red, Bromophenol Blue, Bromoxylenol Blue, Xylenol Orange Tetrasodium Salt, 1-[4-[[4-(dimethylamino)phenyl]azo]phenyl]-2,2,2-trifluoroethanone-, 4-[2-[4-(dimethylamino)phenyl]ethenyl]-2,6-dimethyl-pyrylium perchlorate, and 1-amino-4-(4-decylphenylazo)-naphthalene.

The chemoresponsive dye may be, for example, a solvatochromic dye or a vapochromic dye. Solvatochromic dyes may change color depending upon the local polarity of their liquid micro-environment. Vapochromic dyes may change color depending upon the local polarity of their gaseous micro-environment. Most dyes are solvatochromic and/or vapochromic to some extent; however, some are much more responsive than others, especially those that can have strong dipole-dipole interactions. Examples of solvatochromic dyes include Reichardt's dyes, Nile Red, Fluorescein, and polypyrrolic dyes.

An array that includes a pH sensitive dye and/or a solvatochromic or vapochromic dye may be useful in differentiating analytes that do not bind to, or bind only weakly to, metal ions. Such analytes include acidic compounds, such as carboxylic acids, and certain organic compounds lacking ligatable functionality. Examples of organic compounds lacking ligatable functionality include simple alkanes, arenes, and some alkenes and alkynes, especially if sterically hindered. Examples of organic compounds lacking ligatable functionality also include molecules that are sufficiently sterically hindered to preclude effective ligation. Arrays that include a pH sensitive and/or a solvatochromic or vapochromic dye are described, for example, in U.S. Patent Application Publication No. 2003/0143112 to Suslick et al., which is incorporated by reference herein.

The chemoresponsive dye may be, for example, a redox sensitive dye that undergoes a change in spectral properties depending upon its oxidation state. Examples of dyes that are redox sensitive include redox indicators such as methylene blue, naphthol blue-black, brilliant ponceau, .alpha.-naphthoflavone, basic fuchsin, quinoline yellow, thionin acetate, methyl orange, neutral red, diphenylamine, diphenylaminesulfonic acid, 1,10-phenanthroline iron(II), permanganate salts, silver salts, and mercuric salts.

The chemoresponsive dye may be, for example, a metal ion sensitive dye that undergoes a change in spectral properties in the presence of metal ions. Examples of dyes that are metal ion sensitive include metal ion indicator dyes such as eriochrome black T, murexide, 1-(2-pyridylazo)-2naphthol, and pyrocatechol violet.

The chemoresponsive colorant may be a chemoresponsive pigment. In some cases, the chemoresponsive pigment is a porous pigment. A porous pigment particle has a chemoresponsive surface area that is much greater than the chemoresponsive surface area of a corresponding nonporous pigment particle. Examples of porous pigments include porous calcium carbonate, porous magnesium carbonate, porous silica, porous alumina, porous titania, and zeolites.

The chemoresponsive colorant may be a chemoresponsive nanoparticle. A chemoresponsive nanoparticle may be a discrete nanoparticle, or it may be formed from nanoparticle-forming ions or molecules. The nanoparticle may be in a variety of forms, including a nanosphere, a nanorod, a nanofiber, and a nanotube. Examples of chemoresponsive nanoparticles include nanoporous porphyrin solids, semiconductor nanoparticles such as quantum dots, and metal nanoparticles.

The use of more than one type of chemoresponsive colorant may expand the range of analytes to which the array is sensitive, may improve sensitivity to some analytes, and/or may increase the ability to discriminate between analytes. In some cases, a colorimetric array includes 2 to 1,000 sensors, 4 to 500 sensors, or 8 to 250 sensors. In certain cases, a colorimetric array includes from 10 to 100 sensors (e.g., 16 to 80 sensors, 36 sensors, or 60 sensors). Each sensor in a colorimetric array may include a different colorant. However, it may be desirable to include duplicate sensors that include the same colorant. Duplicate sensors may be useful, for example, to provide redundancy to the array and/or to serve as an indicator for quality control. Table 1 lists exemplary chemoresponsive colorants for a colorimetric sensor array having 36 sensors.

TABLE 1

Exemplary chemoresponsive colorants for a colorimetric sensor array.

| No. | Colorant |
|---|---|
| 1 | 5,10,15,20-Tetraphenyl-21H,23H-porphine zinc |
| 2 | 5,10,15,20-Tetraphenyl-21H,23H-porphine copper(II) |
| 3 | 5,10,15,20-Tetraphenyl-21H,23H-porphine manganese(III) chloride |
| 4 | 2,3,7,8,12,13,17,18-Octaethyl-21H,23H-porphine iron(III) chloride |
| 5 | 5,10,15,20-Tetraphenyl-21H,23H-porphine cobalt(II) |
| 6 | meso-Tetra(2,4,6-trimethylphenyl)porphine |
| 7 | Nitrazine Yellow (basic) |
| 8 | Methyl Red (basic) |
| 9 | Chlorophenol Red (basic) |
| 10 | Napthyl Blue Black |
| 11 | Bromothymol Blue (basic) |
| 12 | Thymol Blue (basic) |
| 13 | m-Cresol purple (basic) |
| 14 | Zinc (II) Acetate with m-Cresol purple (basic) |
| 15 | Mercury (II) Chloride with Bromophenol Blue (basic) |
| 16 | Mercury (II) Chloride with Bromocresol Green (basic) |
| 17 | Lead (II) Acetate |
| 18 | Tetraiodophenolsulfonephthalein |
| 19 | Fluorescein |
| 20 | Bromocresol Green |
| 21 | Methyl Red |
| 22 | Bromocresol Purple |
| 23 | Bromophenol Red |
| 24 | Brilliant Yellow |
| 25 | Silver nitrate + Bromophenol Blue (basic) |
| 26 | Silver nitrate + Bromocresol Green (basic) |
| 27 | Cresol Red (acidic) |
| 28 | Disperse Orange 25 |
| 29 | m-Cresol Purple |
| 30 | Nitrazine Yellow |
| 31 | Cresol Red |
| 32 | Bromocresol Green |
| 33 | Phenol Red |
| 34 | Thymol Blue |
| 35 | Bromophenol Blue |
| 36 | m-Cresol Purple |

For gas or vapor analytes, a gas stream containing the analyte is passed over the array, and images may be obtained before, during and/or after exposure to the gas stream. Preferably, an image is obtained after the sample and the array have equilibrated. If the gas stream is not pressurized, it may be useful to use a miniaturized pump.

For analytes dissolved in a solvent, either aqueous or non-aqueous, the first image may be obtained in air or, preferably, after exposure to the pure carrier solvent that is used of the sample. The second image of the array may be obtained after the start of the exposure of the array to the sample. Preferably an image is obtained after the sample and the array have equilibrated.

Analyzing the differences between the first image and the second image may include quantitative comparison of the digital images before and after exposure to the analyte. Using customized software or standard graphics software such as Adobe® PhotoShop®, a difference map can be obtained by subtracting the first image from the second image. To avoid subtraction artifacts at the periphery of the spots, the center of each spot can be averaged.

Figure 2C:
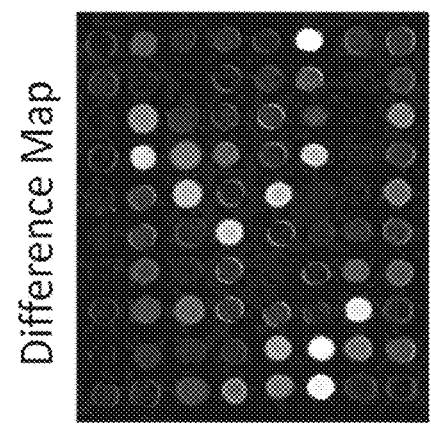
FIG. 2C shows the difference between the colorimetric sensor arrays of FIGS. 2A and 2B.
Figure 2B:
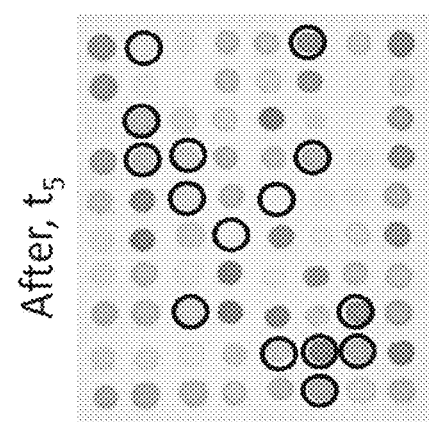
FIG. 2B shows the colorimetric sensor array of FIG. 2A after exposure to *E. coli* 25922 on growth medium for five hours.
Figure 2A:
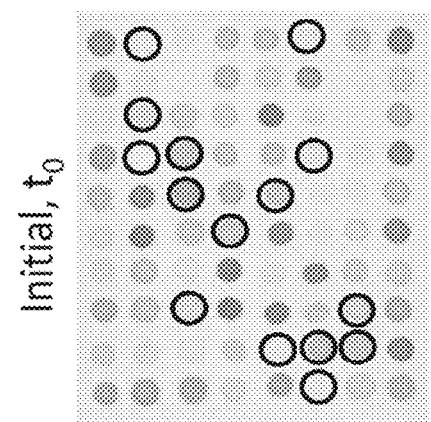
FIG. 2A shows a colorimetric sensor array before exposure to metabolic products of *E. coli* 25922.

FIGS. 2A-2C are images from a colorimetric sensor array, showing the array before exposure to E. coli 25922 (FIG. 2A), after exposure to E. coli 25922 (FIG. 2B), and a difference map of these two images (FIG. 2C). The comparison data obtained from the difference map includes changes in red, green and blue values ($\Delta$RGB) for each spot in the array. The changes in spectral properties that occur upon exposure to an analyte, and the resultant color difference map, can serve as a unique fingerprint for any analyte or mixture of analytes at a given concentration.

In the simplest case, an analyte can be represented by a single 3x vector representing the $\Delta$RGB values for each colorant, where x is the number of colorants as set forth in equation (1). This assumes that equilibration is relatively rapid and that any irreversible reactions between analyte and colorant are slow relative to the initial equilibration time $$\text{Difference vector} = \Delta R1, \Delta G1, \Delta B1, \Delta R2, \Delta G2, \Delta B2, \ldots \Delta Rx, \Delta Gx, \Delta Bx \quad (1)$$

Alternatively, the temporal response of the analyte can be used to make rapid identification, preferably using a "time-stack vector" of $\Delta$RGB values as a function of time. In equation 2, a time-stack vector is shown for an array of 36 colorants at times m, n, and finally z, all using the initial scan as the baseline for the differences in red, green and blue values:

$$\text{Time stack vector} = \Delta R1m, \Delta G1m, \Delta B1m, \Delta R2m, \Delta G2m, \Delta B2m, -\Delta R36m, \Delta G36m, \Delta B36m, \ldots \Delta R1n, \Delta G1n, \Delta B1n, \ldots \Delta R36m, \Delta G36m, \Delta B36m, \ldots \Delta R36z, \Delta G36z, \Delta B36z \quad (2)$$

Accordingly, each analyte response can be represented digitally as a vector of dimension 3xz, where x is the number of colorants and z is the number of scans at different times. Quantitative comparison of such difference vectors can be made simply by measuring the Euclidean distance in the 3xz space. Such vectors may then be treated by using chemometric or statistical analyses, including principal component analysis (PCA), hierarchical cluster analysis (HCA) and linear discriminant analysis. Statistical methods suitable for high dimensionality data are preferred. As an example, HCA systematically examines the distance between the vectors that represent each colorant, forming clusters on the basis of the multivariate distances between the analyte responses in the multidimensional ΔRGB color space using the minimum variance ("Ward's") method for classification. A dendrogram can then be generated that shows the clustering of the data from the Euclidean distances between and among the analyte vectors, much like an ancestral tree.

FIGS. 3A-D show the temporal response of four different sensors from the sensor array shown in FIGS. 2A-2C to metabolic products of E. coli 25922. The sample is identified as containing E. coli 25922 by comparison of the temporal responses of the same sensors to a library of responses from known microorganisms.

A colorimetric array may be used to detect analytes in exhaled breath. Detection of compounds in exhaled breath can be useful in detecting infection or disease. The colorimetric detection of ammonia in exhaled breath is described, for example, in U.S. Patent Application Publication No. 2005/0171449 to Suslick et al., which is incorporated by reference herein.

To detect a microorganism by species and strain, a sample including the microorganism is placed in a container including culture medium and a colorimetric array, and the temporal response of the sensors to the metabolic products of the microorganism is monitored. Susceptibility can be assessed by inoculating a growth medium including a substance (e.g., an antibiotic) with a microorganism and monitoring the temporal response of the sensors while also monitoring the response of a control (e.g., no antibiotic).

FIG. 4 depicts exemplary container 400 with colorimetric sensor array 100 for detecting detect a microorganism or its susceptibility. Container 400 may include a solid or liquid culture medium generally known in the art. A sample, such as a fluid sample (e.g., blood, sputum, exhaled breath) from a mammal, a tissue sample from a mammal, or the like, is placed or injected in container 400. Container 400 is sealed, and colorimetric sensor array 100 is exposed to volatile organic compounds emitted from the microorganisms during growth.

Figure 5:
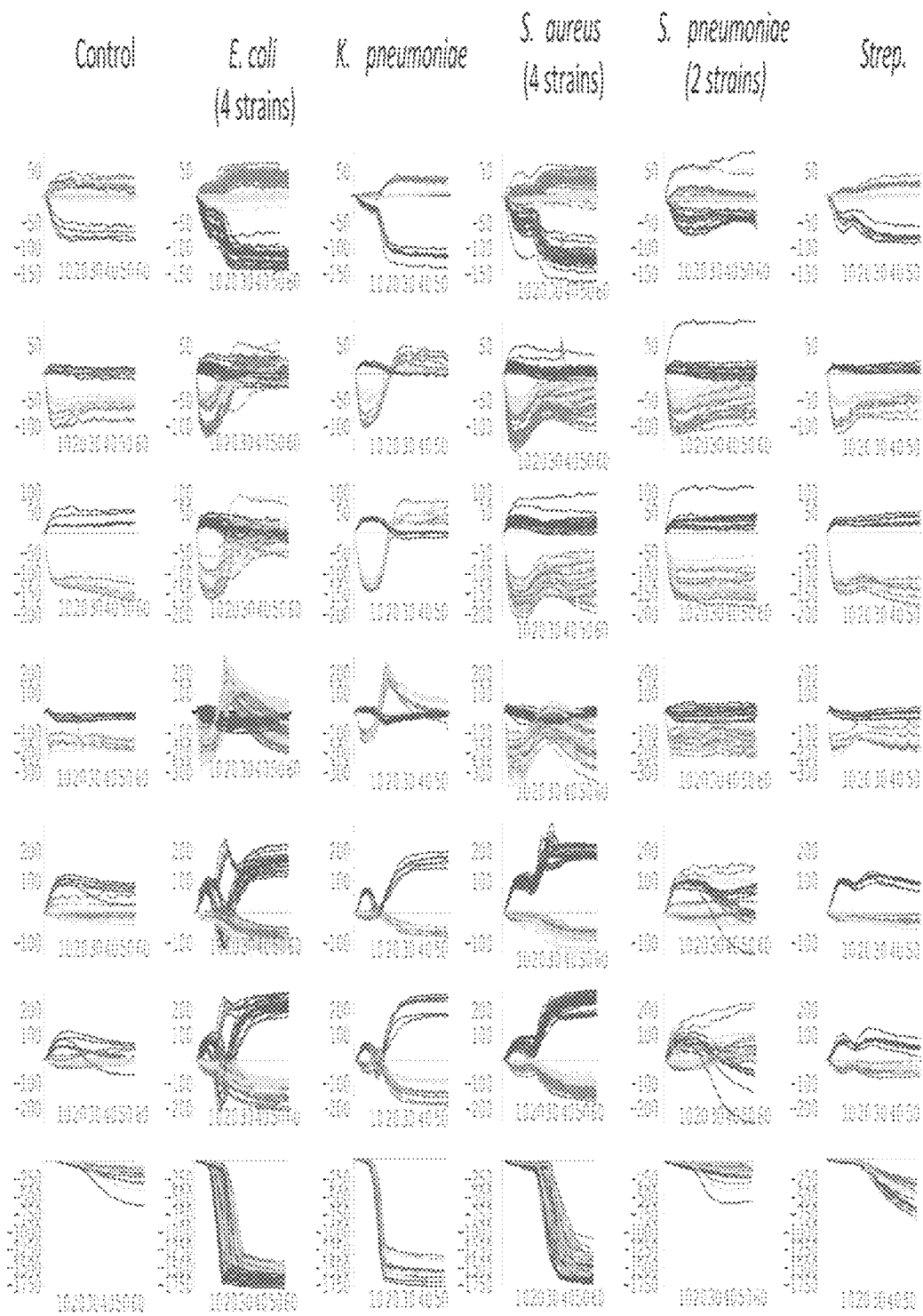
FIG. 5 shows temporal results for various sensors of a colorimetric sensor array used for identification of bacteria.

Identification of species and strain of the microorganism is achieved by comparison of kinetic profiles of the color sensors in a colorimetric sensor array exposed to metabolic products of the microorganism. For illustration purposes, FIG. 5 shows temporal responses of various bacteria for sensors corresponding to those in Table 1, with magnitude of response on the y axis and time on the x axis. Based on low/high inoculum concentration, E. coli was identified in 3-6 hours, K. pneumoniae was identified in 3-5 hours, S. aureus was identified in 3-7 hours, S. pneumoniae was identified in 7-9 hours, and Strep Group A and B was identified in 6-9 hours. Blood culture results show an overall identification accuracy of 99% for various species, including S. aureus (18/19 correct), E. faecalis (4/5 correct), E. faecium (6/6 correct), E. coli (15/15 correct), P. mirabilis (4/4 correct), S. marcescens (5/5 correct), E. cloacae (5/5 correct), K. pneumoniae (17/17 correct), P. aeruginosa (17/17 correct), and blood only (8/8 correct). Table 2 shows accuracy of 99% for identification of various bacterial species.

TABLE 2

Identification of Bacterial Species

| Species | Correct/total | Percent correct |
|---|---|---|
| A. xylosioxidans | 24/24 | 100 |
| B. cepacia | 11/12 | 92 |
| C. diversus | 24/24 | 100 |
| C. Freundii | 17/18 | 94 |
| E. coli | 114/114 | 100 |
| K. pneumonia | 18/18 | 100 |
| M. luteus | 18/18 | 100 |
| P. aeruginosa | 24/24 | 100 |
| P. mirabilis | 24/24 | 100 |
| P. vulgaris | 11/12 | 92 |
| S. aureus | 59/60 | 98 |
| S. epidermidis | 18/18 | 100 |
| S. lugdunesis | 18/18 | 100 |
| S. typhi | 12/12 | 100 |
| Control | 6/6 | 100 |

Figure 6:
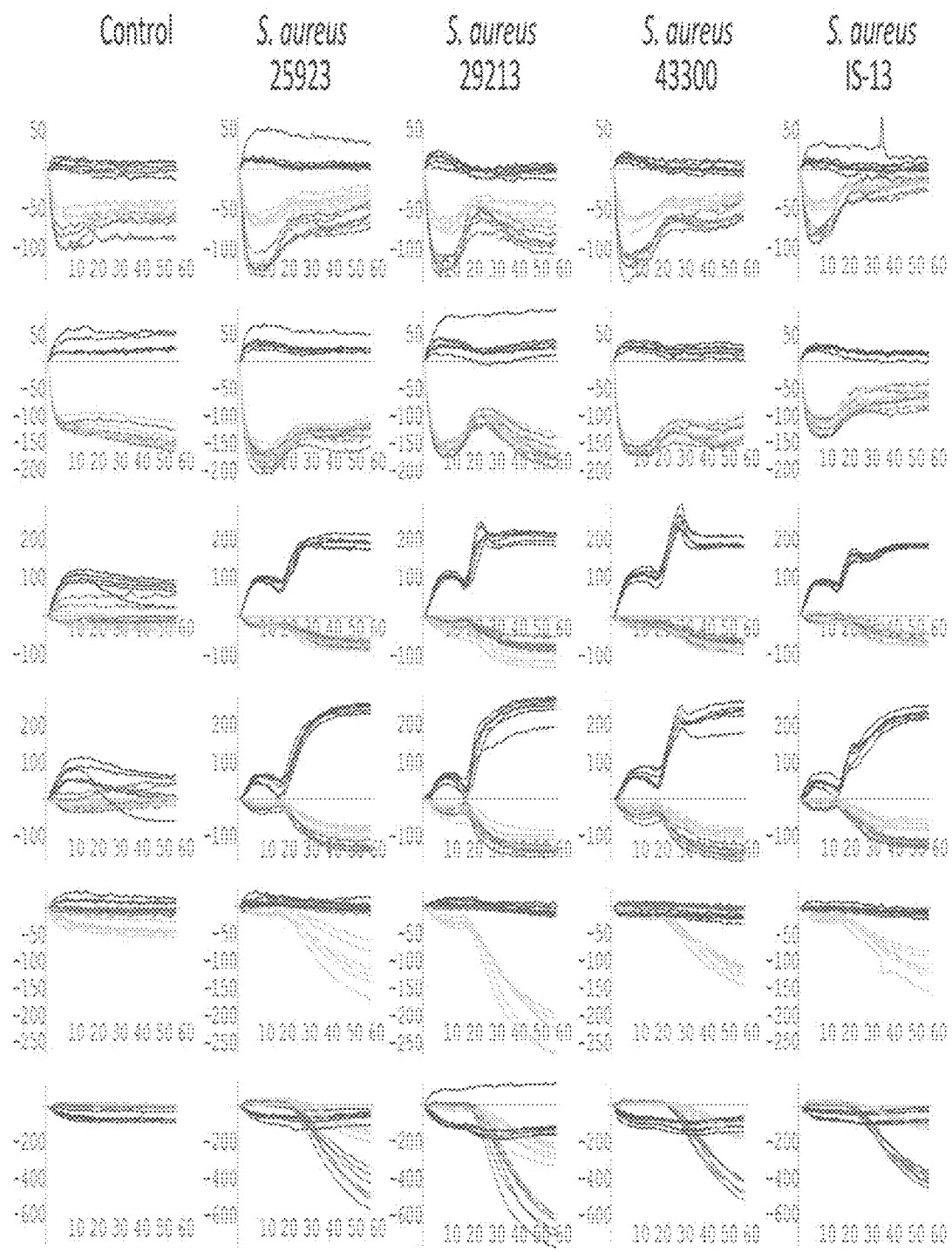
FIG. 6 shows temporal results for various sensors of a colorimetric sensor array used for strain-specific identification of bacteria.

FIG. 6 shows strain-specific sensor patterns for S. aureus 25923, S. aureus 29213, S. aureus 43300, and S. aureus IS-13. Table 3 shows 100% accurate strain identification for 29 out of 31 strains of bacteria. ("IS-# refers to clinical isolate; other data represents ATCC reference strains.)

TABLE 3

Identification of Bacterial Strains.

| Species | Strain | Percent correct |
|---|---|---|
| A. xylosioxidans | IS-30 | 100 |
| A. xylosioxidans | IS-35 | 100 |
| A. xylosioxidans | IS-46 | 100 |
| A. xylosioxidans | IS-55 | 100 |
| P. aeruginosa | IS-15 | 100 |
| P. aeruginosa | IS-65 | 100 |
| P. aeruginosa | IS-22 | 100 |
| P. aeruginosa | IS-36 | 100 |
| S. aureus | 25923 | 100 |
| S. aureus | 29213 | 100 |
| S. aureus | 43300 | 100 |
| S. aureus | IS-13 | 100 |
| S. aureus | IS-38 | 100 |
| S. aureus | IS-43 | 100 |
| S. aureus | IS-70 | 100 |
| E. coli | 25922 | 100 |
| E. coli | 35218 | 100 |
| E. coli | 760728 | 94 |
| E. coli | IS-39 | 12.5 |
| E. coli | IS-44 | 100 |
| C. diversus | IS-01 | 100 |
| C. diversus | IS-28 | 100 |
| C. diversus | IS-31 | 100 |
| C. diversus | IS-33 | 100 |

Figure 7:
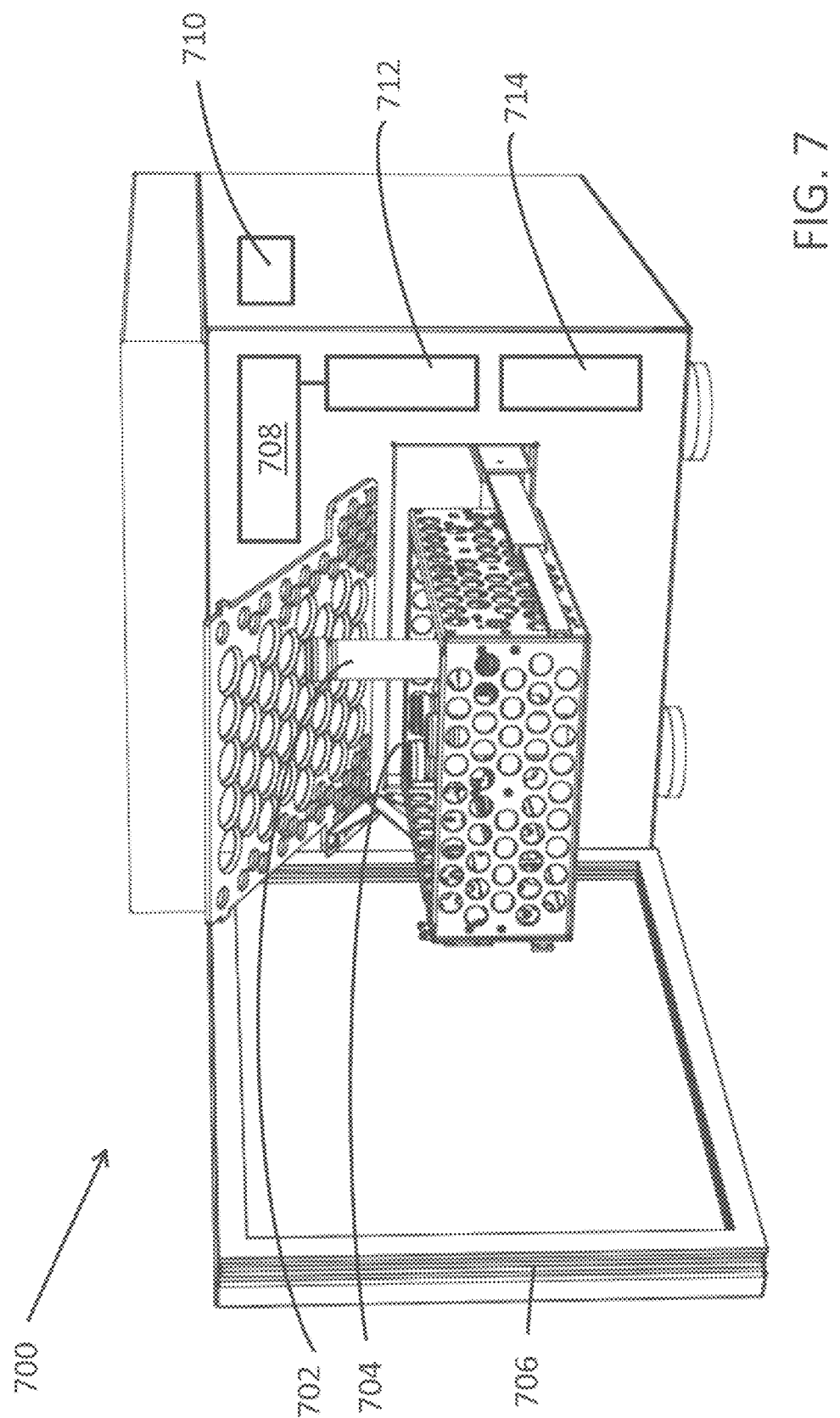
FIG. 7 depicts an apparatus for automatic identification of microorganisms.

FIG. 7 depicts apparatus 700 for automated identification of microorganisms by species and strain. Containers 702 for culturing samples including microorganisms in the presence of colorimetric sensor array 704 are positioned in housing 706 of apparatus 700. Containers 702 may be of various designs configured to hold liquid or solid media, fluid or solid samples, or any combination thereof. Housing 706 also includes detector 708 operable to detect a change in one or more color components of each sensor of each sensor array 704. Detector 708 may be, for example, a scanner (e.g., a flatbed scanner). Apparatus 700 may also include thermostat 710 operatively coupled to a controlled-environment portion for incubating the samples.

Apparatus 700 may also include processor 712 configured to operate the detector at selected time intervals, recording data to be manipulated by processor to generate temporal and/or static color response patterns. Apparatus 700 may also include memory storage device 714 operatively coupled to the processor that stores a multiplicity of temporal and/or static color response patterns of known species and/or strains of microorganisms (e.g., bacteria, yeast, protozoa). Thus, the system is operable to generate a temporal and/or static color response pattern of a sample including a microorganism, and automatically identify the microorganism (e.g., by species and strain) by comparing the generated color response pattern with the stored multiplicity of temporal and/or static color response patterns (e.g., the "library") of known species and/or strains of microorganisms. Comparing the generated color response pattern with the library of known species and/or strains of microorganisms may be achieved by one of a number of statistical methods generally known in the art.

Apparatus 700 is also operable to assess susceptibility of the microorganism with a second colorimetric sensor array. In some cases, the susceptibility assay follows species identification (e.g., in a blood culture without requiring growth of colonies in plate media), thus allowing rapid and cost effective determination of susceptibility. In certain cases, susceptibility is identified directly using the specimen obtained from a blood culture, allowing both species identification and susceptibility assay to be complete less than 24 hours (including 10 hours for species/strain ID and a further 6-8 hours for susceptibility assay).

Figure 8:
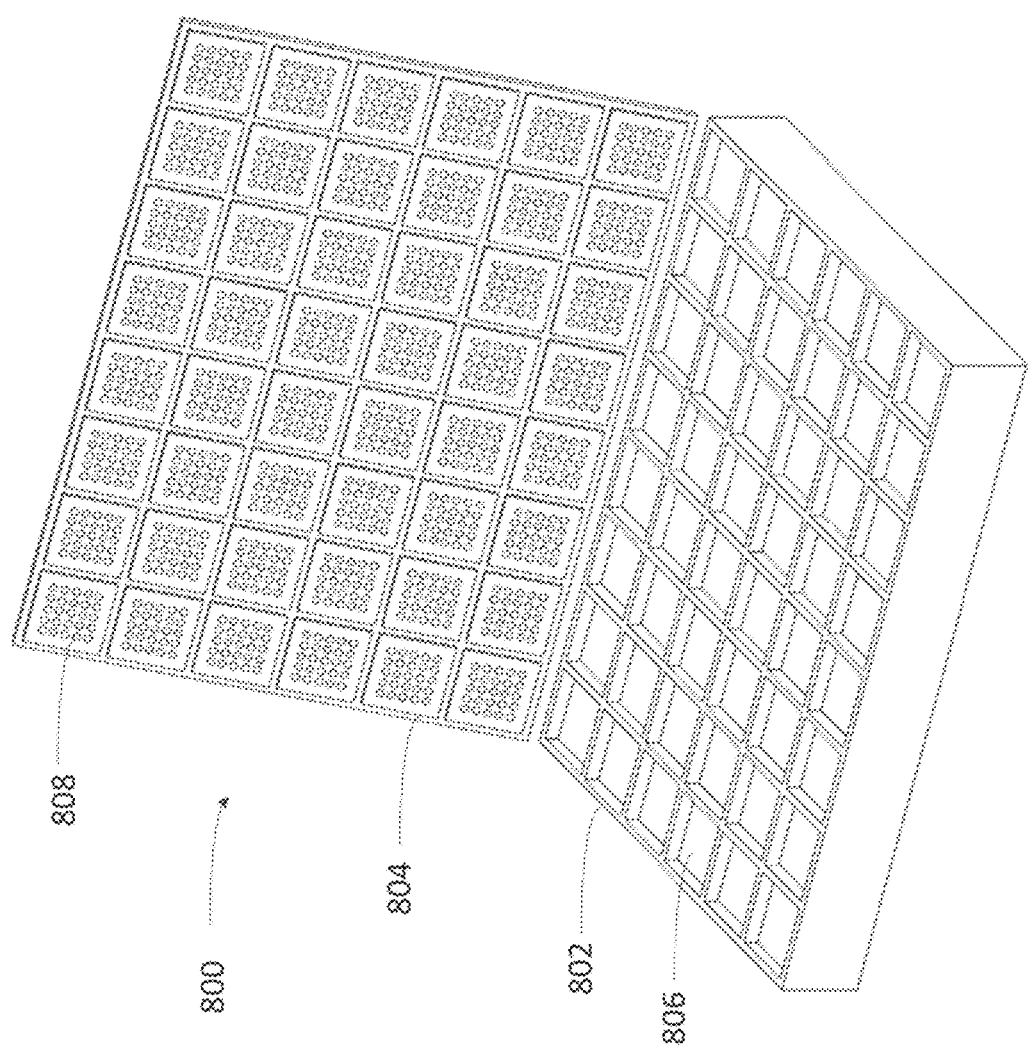
FIG. 8 depicts an apparatus for assessing antibiotic susceptibility of a microorganism.

FIG. 8 depicts container 800 configured for use to assess susceptibility of microorganisms. Container 800 includes base 802 and lid 804, with plates 806 positioned in base 802 opposite colorimetric sensor arrays 808 on lid 804. Microorganisms may be placed in contact with growth medium (e.g., a solid growth medium) in plates 806. A substance (e.g., a drug such as an antibiotic) may be added to the growth medium. In one example, rows and columns of plates 802 in container 800 may be used for different microorganisms, different substances (e.g., drugs effective to kill the microorganisms), or different concentrations of substances. After samples are loaded on plates 802, lid 804 is positioned over base 802, such that each colorimetric sensor array 808 is proximate a plate 806. Susceptibility is assessed via temporal response of the sensors in colorimetric sensor arrays. Container 800 can be positioned in an apparatus (e.g., apparatus 700) for automated assessment of susceptibility.

In other embodiments, susceptibility is assessed by preparing a matrix of well including a mixture of growth media and an antibiotic at a specific concentration into which a microorganism is inoculated. A colorimetric sensor array is positioned proximate the well matrix, and color response is monitored to determine if the microorganism inoculated into the well grows or is susceptible to the antibiotic in the well.

Figure 9:
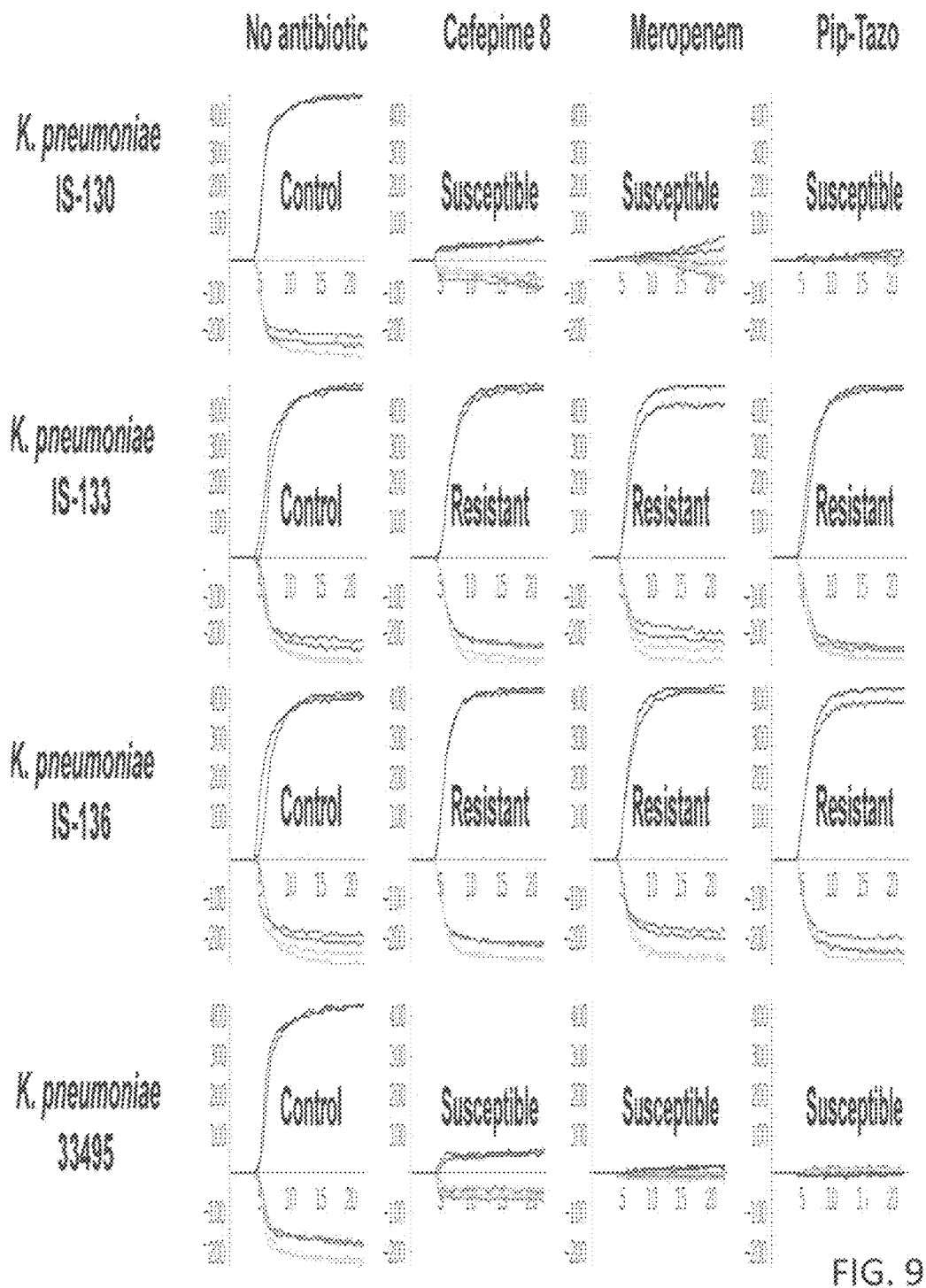
FIG. 9 shows temporal results of susceptibility tests for various sensors of a colorimetric sensor array for identified strains of *K. pneumoniae*.
Figure 10:
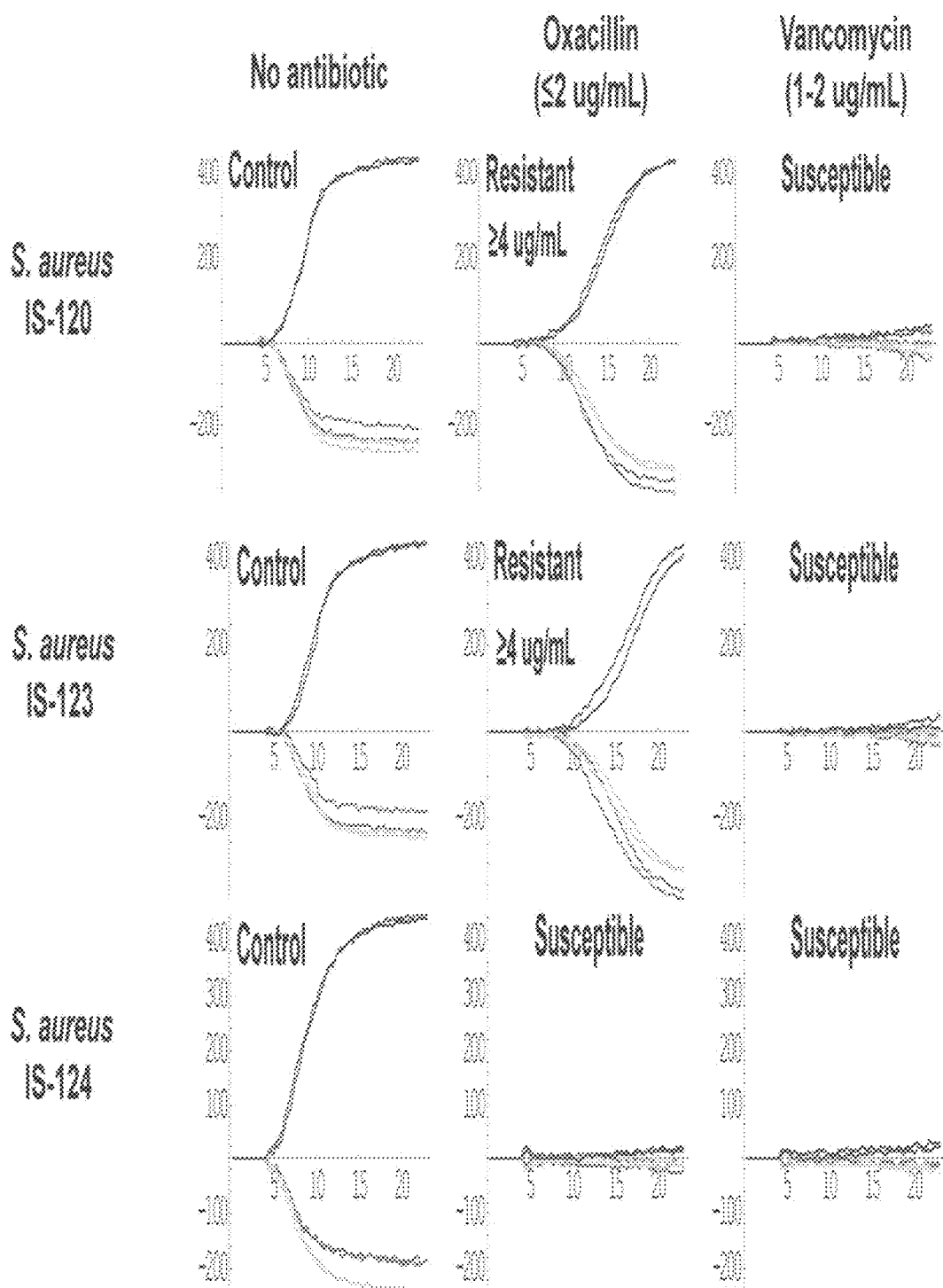
FIG. 10 shows temporal results of susceptibility tests for various sensors of a colorimetric sensor array for identified strains of *S. aureus*.

FIG. 9 shows susceptibility of *K. pneumoniae* strains obtained in 6 hours in Muller-Hinton agar (x axis indicates time in hours). Susceptibility is indicated by a lack of metabolic products compared to controls (no antibiotic). Antibiotic resistance is indicated by the presence of metabolic products on a scale comparable to that of the control. FIG. 10 shows susceptibility of *S. aureus* strains obtained in 6 hours in Muller-Hinton agar.

In another susceptibility test, three strains of *K. pneumoniae* were inoculated onto the solid growth media with no antibiotic (control), piperacillin/tazobactam (PIP/TAZO) at concentrations of 16 ug/ml and 4 ug/ml, Cefepime at 8 ug/ml and Meropenem at 1 ug/ml. For *K. pneumoniae* IS-007, results show susceptibility to PIP/Tazo (at 16 and 4 ug/ml) and Meropenem (at 1 ug/ml) and resistance to Cefepime at 8 ug/ml. These results are in agreement with known susceptibility information that this strain is resistant to Cefepime below 64 ug/ml & susceptible to PIP/Tazo at 4 ug/ml, Cefepime <0.25 ug/ml. *K. pneumoniae* IS-020 was susceptible to all 3 antibiotics in agreement with known susceptibility information that this strain is susceptible to PIP/Tazo at <4 ug/ml, Cefepime<1 ug/ml and Meropenem at <0.25 ug/ml). *K. pneumoniae* IS-133 is known to be resistant at concentrations of PIP/Tazo below 128 ug/ml, Cefepime below 64 ug/ml and Meropenem below 16 ug/ml.

In another susceptibility test, three strains of *S. aureus* were inoculated onto the solid growth media. *S. aureus* IS-120 shows resistance to Oxacillin (at 2 ug/ml) and susceptibility to Vancomycin (at 1-2 ug/ml). These results are in agreement with known susceptibility information that this strain is resistant to Oxacillin below 4 ug/ml and susceptible to Vancomycin. *S. aureus* IS-123 shows resistance to Oxacillin (at 2 ug/ml) and susceptibility to Vancomycin (at 1-2 ug/ml). These results are in agreement with known susceptibility information that this strain is resistant to Oxacillin below 4 ug/ml and susceptible to Vancomycin. *S. aureus* IS-124 was susceptible to both antibiotics in agreement with known susceptibility information that this strain is susceptible to Oxacillin and Vancomycin.

From over 900 susceptibility tests with 98 different bacterial strains, it has been demonstrated that strain-specific susceptibility to antibiotic therapy can be achieved in a range of 6 to 8 hours. Thus, together with strain-specific identification within 8 to 16 hours, strains can be identified and susceptibility can be assayed in 28 hours or less, typically 24 hours or less.

Other embodiments are within the claims.

Although the above description and the attached claims disclose a number of embodiments of the present invention, other alternative aspects of the invention are disclosed in the following further embodiments.

Embodiment 1

A method comprising:
culturing a sample comprising a species of bacteria in the presence of a colorimetric sensor array, thereby exposing sensors in the colorimetric sensor array to volatile organic compounds produced by the bacteria; and
identifying the bacteria by species and strain based on the response of the sensors in the colorimetric sensor array to the volatile organic compounds produced by the bacteria.

Embodiment 2

The method of embodiment 1, wherein identifying the bacteria by species and strain comprises assessing a response of the sensors over time.

Embodiment 3

The method of embodiment 1, wherein identifying the bacteria by species and strain comprises differentiating between strains of the same species of bacteria.

Embodiment 4

The method of embodiment 1, wherein identifying the bacteria by species and strain comprises identifying a substance-resistant strain of a species of bacteria.

Embodiment 5

The method of embodiment 1, wherein identifying the bacteria by species and strain comprises identifying a strain of bacteria selected from species consisting of Staphylococcus aureus, Staphylococcus epidermidis, Staphylococcus sciuri, Pseudomonas aeruginosa, Enterococcus faecium, Enterococcus faecalis, Escherichia coli, Klebsiella pneumoniae, Streptococcus pneumoniae, Streptococcus pyrogenes, Vibrio cholera, Achromobacter xylosoxidans, Burkholderia cepacia, Citrobacter diversus, Citrobacter freundii, Micrococcus leuteus, Proteus mirabilis, Proteus vulgaris, Staphylococcus lugdunegis, Salmonella typhi, Streptococcus Group A, Streptococcus Group B, S. marcescens, Enterobacter cloacae, Bacillus anthracis, Bordetella pertussis, Clostridium sp., Clostridium botulinum, Clostridium tetani, Corynebacterium diphtheria, Moraxalla (Brauhamella) catarrhalis, Shigella spp., Haemophilus influenza, Stenotrophomonas maltophili, Pseudomonas perolens, Pseuomonas fragi, Bacteroides fragilis, Fusobacterium sp. Veillonella sp., Yersinia pestis, and Yersinia pseudotuberculosis.

Embodiment 6

The method of embodiment 1, wherein identifying the bacteria by species and strain comprises identifying an antibiotic-resistant mutant.

Embodiment 7

The method of embodiment 1, wherein identifying the bacteria by species and strain comprises identifying a strain selected from the group consisting of S. aureus 25923, S. aureus 29213, S. aureus 43300, S. aureus IS-13, S. aureus IS-38, S. aureus IS-43, S. aureus IS-70, S. aureus IS-120, S. aureus IS-123, S. aureus IS-124, methicillin-resistant S. aureus 33591, S. epidermidis 35984, S. sciuri 49575, P. aeruginosa 10145, P. aeruginosa IS-15, P. aeruginosa IS-65, P. aeruginosa IS-22, P. aeruginosa IS-36, P. aeruginosa 27853, E. faecium 19434, E. faecalis 23241, vancoymcin-resistant E. faecalis 51299, E. coli 25922, E. coli 53502, E. coli 35218, E. coli 760728, E. coli IS-39, E. coli IS-44, A. xylosoxidans IS-30, A. xylosoxidans IS-35, A. xylosoxidans IS-46, A. xylosoxidans IS-55, C. diversus IS-01, C. diversus IS-28, C. diversus IS-31, C. diversus IS-33, K. pneumoniae IS-130, K. pneumoniae IS-133, K. pneumoniae IS-136, K. pneumoniae 33495, B. anthrax Ames, B. anthrax UM23CL2, B. anthrax Vollum, Y. pestis CO92, Y. pestis Java 9, S. epidermis 12228, S. epidermis IS-60, S. epidermis IS-61, P. miribilis IS-18, P. miribilis IS-19, P. miribilis 12453, S. marcescens IS-48, S. marcescens IS-05, and S. marcescens 13880.

Embodiment 8

The method of embodiment 1, wherein the bacteria are identified by species and strain in less than 64 hours, less than 48 hours, less than 36 hours, less than 24 hours, less than 12 hours, less than 10 hours, less than 8 hours, less than 6 hours, or less than 4 hours.

Embodiment 9

The method of claim 1, wherein the sample comprises up to 10 colony forming units, up to 100 colony forming units, up to 1000 colony forming units, or over 1000 colony forming units of the bacteria.

Embodiment 10

The method of embodiment 1, wherein culturing the bacteria comprises culturing the bacteria on a solid medium or in a liquid medium.

Embodiment 11

The method of embodiment 1, wherein the response of each sensor comprises a change in one or more color components of the sensor.

Embodiment 12

The method of embodiment 1, wherein the temporal and/or static response of the sensors yields a temporal or static color response pattern of the bacteria.

Embodiment 13

The method of embodiment 12, wherein identifying the bacteria by species and strain comprises comparing the temporal and/or static color pattern of the bacteria with a library of temporal and/or static color response patterns characteristic of known strains of bacteria.

Embodiment 14

The method of embodiment 1, further comprising assessing susceptibility of the bacteria to a substance based on the response of the sensors in the colorimetric sensor array to the volatile organic compounds produced by the bacteria.

Embodiment 15

The method of embodiment 14, wherein the susceptibility of the bacteria to the substance is assessed within 64 hours, within 48 hours, within 36 hours, within 24 hours, within 12 hours, within 10 hours, within 8 hours, within 6 hours, or within 4 hours after identification of the bacteria by species and strain.

Embodiment 16

The method of embodiment 14, wherein the substance is a medication approved for use by humans.

Embodiment 17

The method of embodiment 1, further comprising collecting the bacteria from a substrate before culturing the bacteria.

Embodiment 18

The method of embodiment 17, wherein the substrate is selected from the group consisting of woven or nonwoven fabric, paper, metal, and plastic.

Embodiment 19

The method of embodiment 1, further comprising collecting the bacteria from a mammal before culturing the bacteria.

Embodiment 20

The method of embodiment 18, wherein the mammal is a human.

Embodiment 21

The method of embodiment 20, wherein collecting the bacteria from the mammal comprises collecting a fluid sample or a tissue sample from the mammal, wherein the fluid sample comprises a gas, a liquid, or a combination thereof.

Embodiment 22

The method of embodiment 21, wherein the fluid sample comprises blood.

Embodiment 23

The method of embodiment 21, wherein the fluid sample comprises exhaled mammalian breath.

Embodiment 24

The method of embodiment 19, further comprising identifying a substance to which the bacteria are susceptible based on the response of the sensors in the colorimetric sensor array to the volatile organic compounds produced by the bacteria, wherein the substance is a medication approved for use by animals or humans.

Embodiment 25

The method of embodiment 24, further comprising administering a dose of the substance to the mammal from which the bacteria was collected, wherein the dose is effective to reduce the number of the identified bacteria in the mammal.

Embodiment 26

A method comprising:
culturing a multiplicity of samples, each sample comprising bacteria of a selected strain, and each sample being cultured independently in the presence of a colorimetric sensor array, thereby exposing sensors in each colorimetric sensor array to volatile organic compounds produced by the bacteria of a single sample; and
identifying, in at least 90% of the samples, at least 92% of the samples, at least 94% of the samples, at least 96% of the samples, at least 98% of the samples, or at least 99% of the samples, the presence of the selected strain of bacteria based on the response of the sensors in each colorimetric sensor array to the volatile organic compounds produced by the bacteria sample in the presence of the respective colorimetric sensor array.

Embodiment 27

A method of reducing a bacterial population in a mammal showing symptoms of infection, the method comprising:
collecting a sample of bacteria from the mammal;
culturing some of the bacteria in the presence of a colorimetric sensor array, thereby exposing sensors in the colorimetric sensor array to volatile organic compounds produced by the bacteria;
identifying susceptibility of the bacteria to a substance based on the response of the sensors in the colorimetric sensor array to the volatile organic compounds produced by the bacteria; and
administering a dose of the substance to the mammal, wherein the dose is effective to reduce the number of the identified bacteria in the mammal.

Embodiment 28

The method of embodiment 27, further comprising identifying the bacteria by species and strain based on the response of the sensors in the colorimetric sensor array to the volatile organic compounds produced by the bacteria before identifying the susceptibility of the bacteria to the substance.

Embodiment 29

The method of embodiment 28, further comprising selecting the substance based on the identified species and strain of the bacteria.

Embodiment 30

The method of embodiment 27, wherein collecting the sample of bacteria from the mammal comprises collecting a fluid sample or a tissue sample from the mammal, wherein the fluid sample comprises a gas, a liquid, or a combination thereof.

Embodiment 31

The method of embodiment 30, wherein the fluid sample comprises blood.

Embodiment 32

The method of embodiment 30, wherein the fluid sample comprised exhaled mammalian breath.

Embodiment 33

The method of embodiment 27, wherein the mammal is a human.

Embodiment 34

The method of embodiment 27, wherein the mammal is showing symptoms of bacteremia.

Embodiment 35

A substrate comprising a multiplicity of colorimetric sensors, each colorimetric sensor comprising an indicator selected to change color in the presence of at least one volatile organic compound, wherein the substrate is configured to be positioned proximate a growth medium comprising bacteria, and exposure of the multiplicity of colorimetric sensors to volatile organic compounds produced by the bacteria allows identification of the bacteria by species and strain based on the response of the sensors in the colorimetric sensor array to the volatile organic compounds produced by the bacteria.

Embodiment 36

The substrate of embodiment 35, wherein the substrate comprises at least 36 colorimetric sensors, at least 48 colorimetric sensors, at least 60 colorimetric sensors, or at least 80 colorimetric sensors.

Embodiment 37

A system comprising:
a substrate comprising a multiplicity of colorimetric sensors, each colorimetric sensor comprising an indicator selected to change color in the presence of at least one volatile organic compound, wherein the substrate is configured to be positioned proximate a growth medium comprising bacteria, and exposure of the multiplicity of colorimetric sensors to volatile organic compounds produced by the bacteria allows identification of the bacteria by species and strain based on the response of the sensors in the colorimetric sensor array to the volatile organic compounds produced by the bacteria; and
a detector, wherein the detector is operable to detect a change in one or more color components of each sensor.

Embodiment 38

The system of embodiment 37, further comprising a processor, wherein the processor is configured to operate the detector at selected time intervals.

Embodiment 39

The system of embodiment 37, wherein the detector comprises a scanner.

Embodiment 40

The system of embodiment 38, wherein the processor is further configured to form a temporal or static color response pattern of the bacteria based on operation of the detector at selected time intervals.

Embodiment 41

The system of embodiment 37, further comprising a memory storage device coupled to the processor and comprising a library of temporal and/or static color response patterns characteristic of known strains of bacteria.

Embodiment 42

The system of embodiment 41, wherein the processor is configured to operate the detector at selected time intervals, to form a temporal or static color response pattern of the bacteria based on operation of the detector at selected time intervals, and to identify the bacteria based on a comparison of the temporal or static color response pattern of the bacteria with the library of temporal and/or static color response patterns characteristic of known strains of bacteria.

Embodiment 43

The system of embodiment 41, wherein the library of temporal and/or static color response patterns characteristic of known strains of bacteria comprises temporal and/or static color response patterns characteristic of known strains of bacteria selected from species consisting of *Staphylococcus aureus, Staphylococcus epidermidis, Staphylococcus sciuri, Pseudomonas aeruginosa, Enterococcus faecium, Enterococcus faecalis, Escherichia coli, Klebsiella pneumoniae, Streptococcus pneumoniae, Streptococcus pyrogenes, Vibrio cholera, Achromobacter xylosoxidans, Burkholderia cepacia, Citrobacter diversus, Citrobacter freundii, Micrococcus leuteus, Proteus mirabilis, Proteus vulgaris, Staphylococcus lugdunegis, Salmonella typhi, Streptococcus* Group A, *Streptococcus* Group B, *S. marcescens, Enterobacter cloacae, Bacillus anthracis, Bordetella pertussis, Clostridium* sp., *Clostridium botulinum, Clostridium tetani, Corynebacterium diphtheria, Moraxalla (Brauhamella) catarrhalis, Shigella* spp., *Haemophilus influenza, Stenotrophomonas maltophili, Pseudomonas perolens, Pseuomonas fragi, Bacteroides fragilis, Fusobacterium* sp. *Veillonella* sp., *Yersinia pestis*, and *Yersinia pseudotuberculosis*.

Embodiment 44

The system of embodiment 41, wherein the library of temporal and/or static color response patterns characteristic of known strains of bacteria comprises temporal and/or static color response patterns characteristic of known strains of bacteria selected from the group of strains consisting of *S. aureus* 25923, *S. aureus* 29213, *S. aureus* 43300, *S. aureus* IS-13, *S. aureus* IS-38, *S. aureus* IS-43, *S. aureus* IS-70, *S. aureus* IS-120, *S. aureus* IS-123, *S. aureus* IS-124, methicillin-resistant *S. aureus* 33591, *S. epidermidis* 35984, *S. sciuri* 49575, *P. aeruginosa* 10145, *P. aeruginosa* IS-15, *P. aeruginosa* IS-65, *P. aeruginosa* IS-22, *P. aeruginosa* IS-36, *P. aeruginosa* 27853, *E. faecium* 19434, *E. faecalis* 23241, vancoymcin-resistant *E. faecalis* 51299, *E. coli* 25922, *E. coli* 53502, *E. coli* 35218, *E. coli* 760728, *E. coli* IS-39, *E. coli* IS-44, *A. xylosoxidans* IS-30, *A. xylosoxidans* IS-35, *A. xylosoxidans* IS-46, *A. xylosoxidans* IS-55, *C. diversus* IS-01, *C. diversus* IS-28, *C. diversus* IS-31, *C. diversus* IS-33, *K. pneumoniae* IS-130, *K. pneumoniae* IS-133, *K. pneumoniae* IS-136, *K. pneumoniae* 33495, *B. anthrax* Ames, *B. anthrax* UM23CL2, *B. anthrax* Vollum, *Y. pestis* CO92, *Y. pestis* Java 9, *S. epidermis* 12228, *S. epidermis* IS-60, *S. epidermis* IS-61, *P. miribilis* IS-18, *P. miribilis* IS-19, *P. miribilis* 12453, *S. marcescens* IS-48, *S. marcescens* IS-05, and *S. marcescens* 13880.

Embodiment 45

A method comprising:
culturing a sample comprising a microorganism in the presence of a colorimetric sensor array, thereby exposing sensors in the colorimetric sensor array to volatile organic compounds produced by the microorganism; and
identifying the microorganism by species and strain based on the response of the sensors in the colorimetric sensor array to the volatile organic compounds produced by the microorganism.

Embodiment 46

The method of embodiment 45, wherein identifying the microorganism comprises assessing a response of the sensors over time.

Embodiment 47

The method of embodiment 45, wherein the microorganism comprises a yeast, a protozoan, or a fungus.

Embodiment 48

The method of embodiment 47, wherein the microorganism is a fungus selected from the group of species consisting of *Microsporum* sp. *Trichophyton* sp. *Epidermophyton* sp., *Sporothrix schenckii*, *Wangiella dermatitidis*, *Pseudallescheria boydii*, *Madurella grisea*, *Histoplasma capsulatum*, *Blastomyces dermatitidis*, *Coccidioides immitis*, *Cryptococcus neoformans*, *Aspergillus fumigatus*, *Aspergillus niger*, and *Candida albicans*.

Embodiment 49

The method of embodiment 45, wherein the microorganism is identified in less than 64 hours, less than 48 hours, less than 36 hours, less than 24 hours, less than 12 hours, less than 10 hours, less than 8 hours, less than 6 hours, or less than 4 hours.

Embodiment 50

The method of embodiment 45, wherein culturing the microorganism comprises culturing the microorganism on a solid medium or in a liquid medium.

Embodiment 51

The method of embodiment 45, wherein the response of each sensor comprises a change in one or more color components of the sensor.

Embodiment 52

The method of embodiment 45, wherein the temporal and/or static response of the sensors yields a temporal or static color response pattern of the microorganism.

Embodiment 53

The method of embodiment 52, wherein identifying the microorganism comprises comparing the temporal and/or static color pattern of the microorganism with a library of temporal and/or static color response patterns characteristic of known microorganisms.

Embodiment 54

The method of embodiment 45, further comprising assessing susceptibility of the microorganism to a substance based on the response of the sensors in the colorimetric sensor array to the volatile organic compounds produced by the microorganism.

Embodiment 55

The method of embodiment 54, wherein the susceptibility of the microorganism to the substance is assessed within 64 hours, within 48 hours, within 36 hours, within 24 hours, within 12 hours, within 10 hours, within 8 hours, within 6 hours, or within 4 hours after identification of the microorganism.

Embodiment 56

The method of embodiment 54, wherein the substance is a medication approved for use by humans.

Embodiment 57

The method of embodiment 45, further comprising collecting the microorganism from a substrate before culturing the microorganism.

Embodiment 58

The method of embodiment 57, wherein the substrate is selected from the group consisting of woven or nonwoven fabric, paper, metal, and plastic.

Embodiment 59

The method of embodiment 45, further comprising collecting the microorganism from a mammal before culturing the microorganism.

Embodiment 60

The method of embodiment 59, wherein the mammal is a human.

Embodiment 61

The method of embodiment 59, wherein collecting the microorganism from the mammal comprises collecting a fluid sample or a tissue sample from the mammal, wherein the fluid sample comprises a gas, a liquid, or a combination thereof.

Embodiment 62

The method of embodiment 61, wherein the fluid sample comprises blood.

Embodiment 63

The method of embodiment 61, wherein the fluid sample comprises exhaled mammalian breath.

Embodiment 64

The method of embodiment 59, further comprising identifying a substance to which the microorganism is susceptible based on the response of the sensors in the colorimetric sensor array to the volatile organic compounds produced by the microorganism, wherein the substance is a medication approved for use by animals or humans.

Embodiment 65

The method of embodiment 64, further comprising administering a dose of the substance to the mammal from which the microorganism was collected, wherein the dose is effective to reduce the number of the identified microorganisms in the mammal.

Embodiment 66

A method comprising:
culturing a multiplicity of samples, each sample comprising a selected microorganism, and each sample being cultured independently in the presence of a colorimetric sensor array, thereby exposing sensors in each colorimetric sensor array to volatile organic compounds produced by the microorganism of a single sample; and identifying, in at least 90% of the samples, at least 92% of the samples, at least 94% of the samples, at least 96% of the samples, at least 98% of the samples, or at least 99% of the samples, the presence of the selected microorganism by species and strain based on the response of the sensors in each colorimetric sensor array to the volatile organic compounds produced by the microorganism in the presence of the respective colorimetric sensor array.

Embodiment 67

A method of reducing a population of a selected microorganism in a mammal carrying the microorganism, the method comprising:
collecting a sample comprising at least one of the selected microorganisms from the mammal;
culturing the microorganism(s) in the presence of a colorimetric sensor array, thereby exposing sensors in the colorimetric sensor array to volatile organic compounds produced by the microorganism(s);
identifying susceptibility of the microorganism(s) to a substance based on the response of the sensors in the colorimetric sensor array to the volatile organic compounds produced by the microorganism(s); and
administering a dose of the substance to the mammal, wherein the dose is effective to reduce the population of the identified microorganism in the mammal.

Embodiment 68

The method of embodiment 67, further comprising identifying the microorganism by species and strain based on the response of the sensors in the colorimetric sensor array to the volatile organic compounds produced by the microorganism before identifying the susceptibility of the microorganism to the substance.

Embodiment 69

The method of embodiment 68, further comprising selecting the substance based on the identified microorganism.

Embodiment 70

The method of embodiment 67, wherein collecting the sample from the mammal comprises collecting a fluid sample or a tissue sample from the mammal, wherein the fluid sample comprises a gas, a liquid, or a combination thereof.

Embodiment 71

The method of embodiment 70, wherein the fluid sample comprises blood.

Embodiment 72

The method of embodiment 70, wherein the fluid sample comprised exhaled mammalian breath.

Embodiment 73

The method of embodiment 67, wherein the mammal is a human.

Embodiment 74

A substrate comprising a multiplicity of colorimetric sensors, each colorimetric sensor comprising an indicator selected to change color in the presence of at least one volatile organic compound, wherein the substrate is configured to be positioned proximate a growth medium comprising a microorganism, and exposure of the multiplicity of colorimetric sensors to volatile organic compounds produced by the microorganism allows identification of the microorganism by species and strain based on the response of the sensors in the colorimetric sensor array to the volatile organic compounds produced by the microorganism.

Embodiment 75

The substrate of embodiment 74, wherein the substrate comprises at least 36 colorimetric sensors, at least 48 colorimetric sensors, at least 60 colorimetric sensors, or at least 80 colorimetric sensors.

Embodiment 76

A system comprising:
a substrate comprising a multiplicity of colorimetric sensors, each colorimetric sensor comprising an indicator selected to change color in the presence of at least one volatile organic compound, wherein the substrate is configured to be positioned proximate a growth medium comprising a microorganism, and exposure of the multiplicity of colorimetric sensors to volatile organic compounds produced by the microorganism allows identification of the microorganism by species and strain based on the response of the sensors in the colorimetric sensor array to the volatile organic compounds produced by the microorganism; and
a detector, wherein the detector is operable to detect a change in one or more color components of each sensor.

Embodiment 77

The system of embodiment 76, further comprising a processor, wherein the processor is configured to operate the detector at selected time intervals.

Embodiment 78

The system of embodiment 77, wherein the detector comprises a scanner.

Embodiment 79

The system of embodiment 78, wherein the processor is further configured to form a temporal or static color response pattern of the microorganism based on operation of the detector at selected time intervals.

Embodiment 80

The system of embodiment 77, further comprising a memory storage device coupled to the processor and comprising a library of temporal and/or static color response patterns characteristic of known microorganisms.

Embodiment 81

The system of embodiment 80, wherein the processor is configured to operate the detector at selected time intervals, to form a temporal or static color response pattern of the microorganism based on operation of the detector at selected time intervals, and to identify the microorganism based on a comparison of the temporal or static color response pattern of the microorganism with the library of temporal and/or static color response patterns characteristic of known microorganisms.

Embodiment 82

The system of embodiment 76, wherein the microorganism comprises a yeast, a protozoan, or a fungus.

Embodiment 83

The system of embodiment 82, wherein the microorganism is a fungus selected from the group consisting of *Microsporum* sp. *Trichophyton* sp. *Epidermophyton* sp., *Sporothrix schenckii*, *Wangiella dermatitidis*, *Pseudallescheria boydii*, *Madurella grisea*, *Histoplasma capsulatum*, *Blastomyces dermatitidis*, *Coccidioides immitis*, *Cryptococcus neoformans*, *Aspergillus fumigatus*, *Aspergillus niger*, and *Candida albicans*.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A method comprising:
    culturing a sample comprising a microorganism in a well containing growth media and an antibiotic, wherein a colorimetric sensor array is positioned proximate to the well, thereby exposing sensors in the colorimetric sensor array to volatile organic compounds produced by the microorganism in the presence of the antibiotic; and
    directly assessing the susceptibility of the microorganism to the antibiotic based on a response of the sensors in the colorimetric sensor array to the volatile organic compounds produced by the microorganism in the presence of the antibiotic.

2. The method of claim 1, wherein the susceptibility of the microorganism to the antibiotic is assessed in less than 24 hours.

3. The method of claim 1, wherein the antibiotic is a medication approved for use by mammals.

4. The method of claim 1, further comprising collecting the microorganism from a substrate before culturing the microorganism.

5. The method of claim 4, wherein the substrate is selected from the group consisting of woven or nonwoven fabric, paper, metal, and plastic.

6. The method of claim 1, further comprising collecting the microorganism from a mammal before culturing the microorganism.

7. The method of claim 6, wherein the mammal is a human.

8. The method of claim 6, wherein collecting the microorganism from the mammal comprises collecting a fluid sample or a tissue sample from the mammal, wherein the fluid sample comprises a gas, a liquid, or a combination thereof.

9. The method of claim 8, wherein the fluid sample comprises blood.

10. The method of claim 1, further comprising identifying an antibiotic to which the microorganism is susceptible based on a temporal response of the sensors in the first colorimetric sensor array to the volatile organic compounds produced by the microorganism in the presence of the antibiotic, wherein the antibiotic is a medication approved for use by animals or humans.

11. The method of claim 10, further comprising administering a dose of the antibiotic to a mammal from which the microorganism was collected, wherein the dose is effective to reduce the number of the identified microorganisms in the mammal.

12. The method of claim 1, further comprising collecting the microorganism from a blood culture or from a plate culture before culturing the sample comprising the microorganism in the well.

13. The method of claim 1, wherein the susceptibility of the microorganism to the antibiotic is assessed without prior identification of the microorganism.

14. A method comprising:
    culturing a test sample comprising a microorganism in a test well containing growth media and an antibiotic, wherein a test colorimetric sensor array is positioned proximate to the test well;
    culturing a control sample comprising the microorganism in a control well containing growth media, wherein a control colorimetric sensor array is positioned proximate to the control well;
    monitoring a color response of each sensor in the test colorimetric sensor array to organic compounds produced by the microorganism in the test well;
    monitoring a color response of each sensor in the control colorimetric sensor array to volatile compounds produced by the microorganism in the control well; and
    comparing the color response of each colorimetric sensor in the test colorimetric sensor array with the color response of each corresponding colorimetric sensor in the control colorimetric sensor array to assess the susceptibility of the microorganism to the antibiotic in the test well.

15. The method of claim 14, wherein the antibiotic is a medication approved for use by mammals.

16. The method of claim 14, further comprising collecting the microorganism from a substrate before culturing the test sample.

17. The method of claim 16, wherein the substrate is selected from the group consisting of woven or nonwoven fabric, paper, metal, and plastic.

18. The method of claim 14, further comprising collecting the microorganism from a mammal before culturing the test sample.

19. The method of claim 18, wherein the mammal is a human.

20. The method of claim 18, wherein collecting the microorganism from the mammal comprises collecting a fluid sample or a tissue sample from the mammal, wherein the fluid sample comprises a gas, a liquid, or a combination thereof.

21. The method of claim 20, wherein the fluid sample comprises blood.

22. The method of claim 14, wherein the susceptibility of the microorganism to the antibiotic in the test well is indicated by a lack of metabolic products compared to the microorganism in the control well.

23. The method of claim 22, wherein, if the microorganism is susceptible to the antibiotic in the test well, further comprising administering a dose of the antibiotic to a mammal from which the microorganism was collected, wherein the dose is effective to reduce the number of the identified microorganisms in the mammal.

24. The method of claim 14, further comprising collecting the microorganism from a blood culture or from a plate culture before culturing the test sample comprising the microorganism in the test well.

25. The method of claim 14, wherein the susceptibility of the microorganism to the antibiotic is assessed without prior identification of the microorganism.

26. The method of claim 14, wherein no antibiotic is present in the control well.

\* \* \* \* \*